US011116823B2

(12) United States Patent
Treco et al.

(10) Patent No.: US 11,116,823 B2
(45) Date of Patent: *Sep. 14, 2021

(54) TREATMENT OF α-GALACTOSIDASE A DEFICIENCY

(71) Applicant: TAKEDA PHARMACEUTICAL COMPANY LIMITED, Osaka (JP)

(72) Inventors: Douglas A. Treco, Arlington, MA (US); Kenneth Loveday, Brookline, MA (US); Marianne Borowski, Glen, NH (US)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 101 days.

This patent is subject to a terminal disclaimer.

(21) Appl. No.: 16/276,039

(22) Filed: Feb. 14, 2019

(65) Prior Publication Data

US 2019/0255156 A1   Aug. 22, 2019

Related U.S. Application Data

(60) Continuation of application No. 15/350,785, filed on Nov. 14, 2016, now Pat. No. 10,245,304, which is a continuation of application No. 14/995,540, filed on Jan. 14, 2016, now Pat. No. 9,523,113, which is a continuation of application No. 12/761,287, filed on Apr. 15, 2010, now Pat. No. 9,267,166, which is a continuation of application No. 11/403,618, filed on Apr. 13, 2006, now Pat. No. 7,833,742, which is a division of application No. 10/423,225, filed on Apr. 25, 2003, now abandoned.

(60) Provisional application No. 60/375,584, filed on Apr. 25, 2002.

(51) Int. Cl.
| | |
|---|---|
| *A61K 38/47* | (2006.01) |
| *A61K 38/00* | (2006.01) |
| *C12Q 1/54* | (2006.01) |

(52) U.S. Cl.
CPC .............. *A61K 38/47* (2013.01); *A61K 38/00* (2013.01); *C12Q 1/54* (2013.01); *C12Y 302/01022* (2013.01); *G01N 2400/10* (2013.01)

(58) Field of Classification Search
CPC .......... A61K 38/47; A61K 38/00; C12Q 1/54; C12Y 302/01022
See application file for complete search history.

(56) References Cited

U.S. PATENT DOCUMENTS

| | | | |
|---|---|---|---|
| 4,407,957 A | 10/1983 | Lim | |
| 4,740,365 A | 4/1988 | Yukimatsu et al. | |
| 4,764,376 A | 8/1988 | Hirsch et al. | |
| 4,764,378 A | 8/1988 | Keith et al. | |
| 5,179,023 A | 1/1993 | Calhoun et al. | |
| 5,272,066 A | 12/1993 | Bergh et al. | |
| 5,298,400 A | 3/1994 | Whiffeld et al. | |
| 5,356,804 A | 10/1994 | Desnick et al. | |
| 5,382,518 A | 1/1995 | Caput et al. | |
| 5,401,650 A | 3/1995 | Desnick et al. | |
| 5,520,639 A | 5/1996 | Peterson et al. | |
| 5,641,670 A | 6/1997 | Treco et al. | |
| 5,654,007 A | 8/1997 | Johnson et al. | |
| 5,658,567 A | 8/1997 | Calhoun et al. | |
| 5,661,132 A | 8/1997 | Eriksson et al. | |
| 5,697,901 A | 12/1997 | Eriksson | |
| 5,704,911 A | 1/1998 | Parsons | |
| 5,733,761 A | 3/1998 | Treco et al. | |
| 5,750,376 A | 5/1998 | Weiss et al. | |
| 5,770,405 A | 6/1998 | Wong-Madden et al. | |
| 5,775,320 A | 7/1998 | Patton et al. | |
| 5,780,014 A | 7/1998 | Eljamal et al. | |
| 5,780,019 A | 7/1998 | Klier et al. | |
| 5,780,045 A | 7/1998 | McQuinn et al. | |
| 5,785,049 A | 7/1998 | Smith et al. | |
| 5,789,247 A | 8/1998 | Ballay et al. | |
| 5,798,113 A | 8/1998 | Dionne et al. | |
| 5,804,413 A | 9/1998 | DeLuca | |
| 5,814,607 A | 9/1998 | Patton | |
| 5,834,251 A | 11/1998 | Maras et al. | |
| 5,843,015 A | 12/1998 | Sage, Jr. et al. | |
| 5,846,233 A | 12/1998 | Lilley et al. | |
| 5,858,751 A | 1/1999 | Paulson et al. | |
| 5,879,327 A | 3/1999 | Moreau DeFarges et al. | |
| 5,968,502 A | 10/1999 | Treco et al. | |
| 6,048,729 A | 4/2000 | Selden et al. | |
| 6,063,630 A | 5/2000 | Treco et al. | |
| 6,083,725 A * | 7/2000 | Selden .................. | C07K 14/61 435/208 |

(Continued)

FOREIGN PATENT DOCUMENTS

| | | |
|---|---|---|
| AU | A1796/88 | 9/1988 |
| AU | B21796/88 | 3/1998 |

(Continued)

OTHER PUBLICATIONS

Eng et al., A Phase 1/2 Clinical Trial of Enzyme Replacement in Fabry Disease:Pharmacokinetic, Substrate Clearance, and Safety Studies, Am. J. Hum. Genet. 68:711-722, 2001 (Year: 2001).*

(Continued)

*Primary Examiner* — Ruth A Davis

(74) *Attorney, Agent, or Firm* — Troutman Pepper Hamilton Sanders LLP

(57) ABSTRACT

The invention provides methods of treating α-galactosidase A deficiency. Dosage forms, methods of administration, and methods of analyzing human α-galactosidase A are also included.

25 Claims, 16 Drawing Sheets

Specification includes a Sequence Listing.

(56) References Cited

U.S. PATENT DOCUMENTS

| | | | |
|---|---|---|---|
| 6,187,305 | B1 | 2/2001 | Treco et al. |
| 6,200,778 | B1 | 3/2001 | Treco et al. |
| 6,214,622 | B1 | 4/2001 | Treco et al. |
| 6,242,218 | B1 | 6/2001 | Treco et al. |
| 6,270,989 | B1 | 8/2001 | Treco et al. |
| 6,410,272 | B1 | 6/2002 | Meyhack et al. |
| 6,458,574 | B1 | 10/2002 | Selden et al. |
| 6,566,099 | B1 | 5/2003 | Selden et al. |
| 6,607,901 | B1 | 8/2003 | Schaffer et al. |
| 7,833,742 | B2 | 11/2010 | Treco et al. |
| 9,523,113 | B2 * | 12/2016 | Treco ............... A61P 13/12 |
| 2003/0049245 | A1 | 3/2003 | Mann et al. |

FOREIGN PATENT DOCUMENTS

| | | |
|---|---|---|
| EP | 0307285 A1 | 3/1989 |
| EP | 0408461 A1 | 1/1991 |
| JP | H01165373 A | 6/1989 |
| JP | H03143393 A | 6/1991 |
| JP | H106503479 A | 4/1994 |
| JP | H108503615 A | 4/1996 |
| WO | 199011353 A1 | 10/1990 |
| WO | 199206187 A1 | 4/1992 |
| WO | 199213067 A1 | 8/1992 |
| WO | 199308292 A1 | 4/1993 |
| WO | 199309222 A2 | 5/1993 |
| WO | 199412628 A1 | 6/1994 |
| WO | 199506478 A1 | 3/1995 |
| WO | 199811206 A2 | 3/1998 |
| WO | 00/53730 A2 | 9/2000 |
| WO | 200053730 A2 | 9/2000 |

OTHER PUBLICATIONS https://my.clevelandclinic.org/health/diseases/16235-fabry-disease, "Fabry Disease", Cleveland Clinic website (Year: 2020).*
Beutler et al., "Purification and Properties of Human .alpha.-Galactosidases", The Journal of Biological Chemistry, vol. 247 (22), pp. 7195-7200, 1972.
Examiner's Answer to Appeal Brief in U.S. Appl. No. 10/165,060 dated May 14, 2009.
European Search Report dated Jul. 3, 2007 for EP Application No. 06025159.2.
Goldman et al., Jam Coll Cardiol, (1986), vol. 7, pp. 1157-1161.
Lemansky et al., "Synthesis and Processing of .alpha.-Galactosidase A in Human Fibroblasts", J. Biol. Chem. 262:2062, 1987.
Mapes et al., Enzyme Replacement in Fabry's Disease and Inborn Error of Metabolism.Science 169:987, 1970.
Marikar et al., "Leaching of Concanavalin a during Affinity Chromatographic Isolation of Cell Surface Glycoproteins from Human Fetal Neurons and Glial Cells", Anal Biochem. 201: 306-310 (1992).
Matsuura et al., "Human .alpha.-galactosidase A: characterization of the N-linked oligosaccharides on the intraceullular and secreted glycoforms overexpressed by Chinese hamster ovary cells", Glycobiology 8: 329-339 (1998).
Matsui et al., Ani Heart J. (1989), vol. 117, pp. 472-474.
May 15, 2017 Office Action issued in connection with JP Application No. 2016-135614.
Medin, "Correction in trans for Fabry disease: Expression, secretion, and uptake of .alpha.-galactosidase A in patient-derived cells driven by a high-titer recombinant retroviral vector", J.A. et al., Proc. Natl. Acad. Sci. USA, 93(15): 7917-7922(1996).
Misra-Press et al., "Complex Alternative Splicing Partially Inactivates the Human Chorionic Somatomammotropin-like (hCS-L) Gene" J. Biol. Chem. 269:23220-23229 (1994).
Mizushima et al., "pEF-BOS, a powerful mammalian expression vector", Nucl. Acids Res. 18:5322 (1990).
Nakao et al., "An atypical Variant of Fabry's Disease in Men with Left Ventricular Hypertrophy", New Engl. J. Mod. 333: 288-293 (1995).

Nolte et al., "Hydrophobic Interaction Chromatography of *Staphylococcus aureus* Delta-Toxin," Infect. Immun., 31(3):1094-1098 (1981).
Parr, "Declaration of Conformity", Biochrom, 1-33, 2001.
Partial European Search Report from European Application Serial No. EP10152432 dated Apr. 6, 2018.
Pastores et al., "Enzyme-replacement therapy for Anderson-Fabry disease," Lancet, 358:601-603 (2001).
PCTIUS97/16603, Search Report, dated May 27, 1998.
Pecceu et al., "Human interleukin 1.beta. fused to the human growth hormone signal peptide is N-glycosylated and secreted by Chinese hamster ovary cells", Gene, vol. 97, pp. 253-258, (1991).
Pierce Tech Tip #6, "Extinction Coefficients", Pierce Biotechnology, Inc., 1-3, 2006.
Rijcken et al., Biochem J. 305: 865-870 (1995).
Sburlati et al., "Synthesis of Bisected Glycoforms of Recombinant IFN-.alpha. by Overexpression of .alpha.-1,4-N-Acetylglucosaminyltransferase III in Chinese Hamster Ovary Cells", Biotechnol. Prog. 14:189-192, 1998, XP-000925916.
Schiffmann et al., "Infusion of .alpha.-galactosidase a reduces tissue globotriaosylceramide storage in patients with Fabry disease", Proc. Natl. Acad. Sci., Jan. 4, 2000; vol. 97, pp. 365-370.
Schiffman et al., "Enzyme Replacement Therapy in Fabry . . . ", JAMA. Jun. 6, 2001; 285(21): 2743.
Selden et al., "Human Growth Hormone as a Receptor Gene in Regulation Studies employing Transient Gene Expression". Mol. Cell. Bioi. 6:3173-3179, 1986.
Shrine, "TKT Files for IPO to Raise 35M as it Nears Human Testing," BioWorld Today, The Daily Biotechnology Newspaper, vol. 7, No. 170, 1996.
S. Sumathy et al., "Expression of Human Growth Hormone in Silkworm . . . " Protein Expression and Purification 7:262-268 (1996).
Sumitomo Dainippon Pharma, Replagal for drip infusion 3.5mg, medicine appended paper, 2015, pp. 1-3.
Talbot, G et al., "Purification and Characterization of Thermostable-Mannanase and I-Galactosidase from Bacillus stearothermophilus," Applied and Environmental Microbiology, vol. 56, No. 11, pp. 3505-3510 (Nov. 1990).
Trimble, et al., "Identification of Distinct Endoglycosidase (Endo) Activities in Flavobacterium meningosepticum; Endo F.sub.1, Endo F.sub.2, and Endo F.sub.3," The Journal of Biological Chemistry, vol. 266, No. 3, pp. 1646-1651 (Jan. 25, 1991).
Tsuji et al., "Signal sequence and DNA-mediated expression of human lysosomal .alpha.-galactosidase A" Eur. J. Biochem. 165:275.
UniProt Accession No. P00924, "UniProtKB/Swiss-Prot entry P00924", 1-8, Jul. 21, 1986.
Ven der Bliek et al., "Genes Amplified and Overexpressed in Human Multidrug-resistant Cell Lines ", Cancer Research 48: 5927-5932 (1988).
Written Opinion for PCT/US00/06118, dated Feb. 28, 2001.
Zapater, et al., "Extracellular I Galactosidase (E.C. 3.2.1.22) from Aspergillus Ficuum NRRL 3135 Purification and Characterization," Preparative Biochemistry, pp. 263-296 (1990).
Okumiya, et al., Japanese Journal of Clinical Medicine 53(12): 2952-2953, 1995.
Extended European Search Report from European Application Serial No. 11151977.3 dated Aug. 2, 2011.
European Search Report from European Application Serial No. EP10152432 dated Aug. 2, 2010.
Bishop et al., "Purification and characterization of human alpha-galactosidase isozymes: comparison of tissue and plasma forms and evaluation of purification methods", Birth Defects Original Article Ser., 16(1):17-32, 1980.
Blam et al., "Addition of growth hormone secretion signal to basic fibroblast growth factor results in cell transformation and secretion of aberrant forms of protein", Oncogene (3)2:129-136 (1988).
Bio-Rad Catalog, "Chromatographic Supports Ion Exchange Chromatography", pp. 2-21, 28-34, 102, and 103; referenced in the text of an Office Action dated Nov. 6, 2000 in U.S. Appl. No. 09/543,921.
Partial European Search Report dated Apr. 27, 2007 from European App. No. EP 04030107.

(56) References Cited

OTHER PUBLICATIONS

Partial European Search Report dated Jul. 3,2007 from European App. No. EP 06025159.
European Search Report dated Sep. 28, 2007 from European App. No. EP 06025159.
Mayes et al., "Endocytosis of Lysosomal Alpha-Galactosidase a by Cultured Fibroblasts from Patients with Fabry Disease", Am. J. Hum. Genet. 34:602-610 (1982).
Wong et al., "Purification and Characterization of I-galactosidase from Azobacter vinelandii", Abstract #K-207, p. 571, Abstracts of the 96.sup.th General Meeting of the American Society for Microbiology (1996).
Australian Official Action dated Sep. 6, 2007 for Application No. 2003228722.
Ashwell et al., "Carbohydrate-Specific Receptors of the Liver" Ann. Rev. Biochem. 51:531-554, 1982.
Beutler, "Gaucher's Disease", New Engl. J. Med. 325: 1354-1360 (1991).
Bishop, David et al., Enzyme Therapy XX: Further for the Differential In Vivo Fate of Human Splenic and Plasma . . . , in Lysomomes and Lysosomal Storage Disease, Rave Press NY, 1981, pp. 381-394.
Bishop et al., "Human .alpha.-galactosidase A: Nucleotide sequence of a cDNA clone encloding the mature enzyme" Proc. Natl. Acad. Sci. USA 83:4859, 1986.
Bishop et al., "Affinity Purification of .alpha.-Galactosidase a from Human Spleen, Placenta, and Plasma with Elimination of Pyrogen Contamination", The Journal of Biological Chemistry, vol. 256(3), pp. 1307-1316 (1981).
Brady et al., "Replacement Therapy for Inherited Enzyme Deficiency" N. Engl. J. Med. 289:9, 1973.
Calhoun et al., "Fabry disease: Isolation of a cDNA clone encoding human .alpha.-galactosidase A", Proc. Natl. Acad. Sci. USA, vol. 82, pp. 7364-7368 (1985).
Cuozzo et al., "Lysine-based Structure Responsible for Selective Mannose Phosphorylation of Cathepsin D and Cathepsin L Defines a Common Structural Motif for Lysosomal Enzyme Targeting", J. Biol. Chem. 273: 1069-21076 (1998).
Delgado et al., Crit. Rev. Ther. Drug Carrier Syst. 9: 249.
Desnick et al., "Enzyme therapy in Fabry disease: Differential in vivo plasma clearance and metabolic effectiveness of plasma and splenic .alpha.-galactosidase A isozymes" Proc. Natl. Acad. Sci. USA 76:5326, 1979.
Desnick et al., ".alpha.-Galactosidase A Deficiency: Fabry Disease: The Metobolic and Molecular Basis of Inherited Disease", Chapter 889, pp. 2741-2784.
Desnick et al., "Enzyme Therapy XVII: Metabolic and Immunologic Evaluation of .alpha.-Galactosidase A Replacement Fabry Disease", Birth Defects, vol. 16(1), pp. 393-413 (1980).
Diment et al., "Generation of Macrophage Variants With 5-Azacytidine: Selection for Mannose Receptor Expression", J. Leukocyte Biol. 41: 485.
Edwards et al., Science 276: 1868-1872 (1997).
English Abstract of JP-A H01-165373.
Eng et al., "A Phase 1/2 Clinical Trail of Enzyme . . . ", Am J Hum Genet. Mar. 2001; 68(3): 71 1.
Eng et al., "Safety and Efficacy of Recombinant Human", N Engl J Med. 2001 ,Jd5; 345(1): 9.
EPO search report for application No. 97942567.5, dated Oct. 7, 2002.
First Office Action from Intellectual Property Office of the People's Republic of China in Application No. 97197909.X, dated Sep. 13, 2002.
Francis et al., "PEGlyation of cytokines and other therapeutic proteins and peptides: the importance of biological optimisation of coupling techniques", Int. J. Hematol 68(1):1-18 (1998).
Garman et al., "The Molecular Defect Leading to Fabry Disease: Structure of Human .alpha.-Galactosidase", J. Mol. Biol., vol. 337, pp. 319-335 (2004).
Grammatikos et al., Biotechnol. Prog. 14: 410-419 (1998).
Hantzopolous et al., Gene, 57: 159 (1987).
Hermentin et al., Glycobiology 6: 217-230 (1996).
Hokke et al., "Sialylated carbohydrate chains of recombinant human glycoproteins expressed in Chinese hamster ovary cells contain trace of N-glyoulmeuraminic acid", Federation of European Biochemical Societies, vol. 27, No. 1, 2, pp. 9-14, (1990).
Hsiung et al., "High-Level Expression, Efficient Secretion and Folding of Human Growth Hormone in *Escherichia coli*" Biotechnology 4: 991-995 (1986).
Ihara et al., "cDNA Cloning, Expression, and Chromosomal Localization of Human N-Acetylglucosaminyltransferase III (Gn-T-111).sup.1", J. Biochem. (Tokyo) 113: 692-698 (1993).
International Search Report for PCT/US00I06118 dated Feb. 23, 2005.
Ioannou et al., "Overexpression of Human a-galactosidase A results in its Intracellular Aggregation, Crystallization in Lysosomes and Selective Secretion", J. Cell Biol. 119:1137, 1992.
Isidoro et al., "Suppression of the 'uncovering' of mannose-6-phosphate residues in lysosomal enzymes in the presence of NH.sub4CI", Eur. J. Biochem. 191:591-597 (1990).
Jenkins et al., "Getting the glycosylation right: Implications for the biotechnology industry", Nature Biotechnology, vol. 14, pp. 975-981 (1996).
Kinstler et al., "Characterization and Stablity of N-terminally PEGylated rhG-CSF", Pharm. Res. 13: 996-1002 (1996).
Komer et al., "Carbohydrate-deficient glycoprotein syndrome type V: Deficiency of dolichyl-P-Glc:Man.sub.9Glc:Man.sub.9GlcNAc.sub.2-PP-dolichyl glucosyltransferase", Proc. Natl. Acad. Sci. USA 95:13200.
Kornfeld & Mellman, "Annual Review of Cell Biology: The Biogenesis of Lysosomes" 5: 483-525 (1989).
Komreich et al., "Nucleotide sequence of the human .alpha.-galactosidase A gene", Nucleic Acids Research; 17:3301, 1998.
Kukuruzinska & Lennon, "Protein N-Glycosylation: Molecular Genetics and Functional Significance", Crit. Rev. Oral. Biol. Med. 9: 415-48 (1998).
LeDonne et al., "Biosynthesis of .alpha.-Galactosidase A in Cultured Change Liver Cells", Arch. Biochem. Biophys.114: 186 (1983).
Lee et al., "A biochemical and pharmacological comparison of enzyme replacement therapies for the glycolipid storage disorder Fabry disease", Glycobiology, vol. 13, No. 4, pp. 305-313 (2003).

* cited by examiner

```
   1 CCGCGGGAAA TTTATGCTGT CCGGTCACCG TGACAATGCA GCTGAGGAAC CCAGAACTAC
  61 ATCTGGGCTG CGCGCTTGCG CTTCGCTTCC TGGCCCTCGT TCCTGGGAC  ATCCCTGGGG
 121 CTAGAGCACT GGACAATGGA TTGGCAAGGA CGCCTACCAT GGGCTGGCTG CACTGGGAGC
 181 GCTTCATGTG CAACCTTGAC TGCCAGGAAG AGCCAGATTC CTGCATCAGT GAGAAGCTCT
 241 TCATGGAGAT GGCAGAGTC  ATGGTCTCAG AAGGGCTGGAA GGATGCAGGT TATGAGTACC
 301 TCTGCATTGA TGACTGTTGG ATGGCTCCCC AAAGAGATTC AGAAGGCAGA CTTCAGGCAG
 361 ACCCTCAGCG CTTTCCTCAT GGGATTCGCC AGCTAGCTAA TTATGTTCAC AGCAAAGGAC
 421 TGAAGCTAGG GATTTATGCA GATGTTGGAA ATAAAACCTG CGCAGGCTTC CCTGGAGTT
 481 TGGATACTA  CGACATTGAT GCCCAGACCT TTGCTGACTG GGGAGTAGAT CTGTAAAAT
 541 TTGATGGTTG TTACTGTGAC AGTTTGGAAA ATTTGGCAGA TGGTTATAAG CACATGTCCT
 601 TGCCCTGAA  AGAAGCATTG AGAAGCATTG TGTACTCCTG TGAGTGGCCT CTTTATATGT
 661 GGCCCTTTCA AAAGCCCAAT TATACAGAAA TCCGACAGTA CTGCAATCAC TGGGAAATT
 721 TTGCTGACAT TGATGATTCC TGGAAAAGTA TAAGAGAGAT CTTGGACTGG ACATCTTTTA
 781 ACCAGGAGAG AATTGTTGAT GTTGCTGGAC CAGGGGGTTG GAATGACCCA GATATGTTAG
 841 TGATTGGCAA CTTTGGCCTC AGCTGGAATC AGCAAGTAAC TCAGATGGCC CTCTGGGCTA
 901 TCATGGCTGC TCCTTTATTC ATGTCTAATG ACCTCCGACA CATCAGCCCT CAAGCCAAAG
 961 CTCTCCTTCA GGATAAGGAC GTAATTGCCA TCAATCAGGA CCCCTTGGGC AAGCAAGGGT
1021 ACCAGCTTAG ACAGGAGAAC AACTTTGAAG TGTGGGAACG ACCTCTCTCA GGCTTAGCCT
1081 GGGCTGTAGC TATGATAAAC CGGCAGGAGA TTGGTGGACC TCGTCTTAT  ACCATCGCAG
1141 TTGCTTCCCT GGGTAAAGGA GTGGCCTGTA ATCCTGCCTG CTTCATCACA CAGCTCCTCC
1201 CTGTGAAAAG GAAGCTAGGG TTCTATGAAT GGACTTCAAG GTTAAGAAGT CACATAAATC
1261 CCACAGGCAC TGTTTGCTT CAGCTAGAAA ATACAATGCA GATGTCATTA AAGACTTAC
1321 TTTAAAAAAA AAAAAAACTC GAG
```

FIG 1

```
Leu Asp Asn Gly Leu Ala Arg Thr Pro Thr Met Gly
Trp Leu His Trp Glu Arg Phe Met Cys Asn Leu Asp
Cys Gln Glu Glu Pro Asp Ser Cys Ile Ser Glu Lys
Leu Phe Met Glu Met Ala Glu Leu Met Val Ser Glu
Gly Trp Lys Asp Ala Gly Tyr Glu Tyr Leu Cys Ile
Asp Asp Cys Trp Met Ala Pro Gln Arg Asp Ser Glu
Gly Arg Leu Gln Ala Asp Pro Gln Arg Phe Pro His
Gly Ile Arg Gln Leu Ala Asn Tyr Val His Ser Lys
Gly Leu Lys Leu Gly Ile Tyr Ala Asp Val Gly Asn
Lys Thr Cys Ala Gly Phe Pro Gly Ser Phe Gly Tyr
Tyr Asp Ile Asp Ala Gln Thr Phe Ala Asp Trp Gly
Val Asp Leu Leu Lys Phe Asp Gly Cys Tyr Cys Asp
Ser Leu Glu Asn Leu Ala Asp Gly Tyr Lys His Met
Ser Leu Ala Leu Asn Arg Thr Gly Arg Ser Ile Val
Tyr Ser Cys Glu Trp Pro Leu Tyr Met Trp Pro Phe
Gln Lys Pro Asn Tyr Thr Glu Ile Arg Gln Tyr Cys
Asn His Trp Arg Asn Phe Ala Asp Ile Asp Asp Ser
Trp Lys Ser Ile Lys Ser Ile Leu Asp Trp Thr Ser
Phe Asn Gln Glu Arg Ile Val Asp Val Ala Gly Pro
Gly Gly Trp Asn Asn Pro Asp Met Leu Val Ile Gly
Asn Phe Gly Leu Ser Trp Asn Gln Gln Val Thr Gln
Met Ala Leu Trp Ala Ile Met Ala Ala Pro Leu Phe
Met Ser Asn Asp Leu Arg His Ile Ser Pro Gln Ala
Lys Ala Leu Leu Gln Asp Lys Asp Val Ile Ala Ile
Asn Gln Asp Pro Leu Gly Lys Gln Gly Tyr Gln Leu
Arg Gln Gly Asp Asn Phe Glu Val Trp Glu Arg Pro
Leu Ser Gly Leu Ala Trp Ala Val Ala Met Ile Asn
Arg Gln Glu Ile Gly Gly Pro Arg Ser Tyr Thr Ile
Ala Val Ala Ser Leu Gly Lys Gly Val Ala Cys Asn
Pro Ala Cys Phe Ile Thr Gln Leu Leu Pro Val Lys
Arg Lys Leu Gly Phe Tyr Glu Trp Thr Ser Arg Leu
Arg Ser His Ile Asn Pro Thr Gly Thr Val Leu Leu
Gln Leu Glu Asn Thr Met Gln Met Ser Leu Lys Asp
Leu Leu
```

FIG. 2

— SampleName; DRX005B Ref Std Description 126-0800-022
   Date Acquired 3/21/02 12:27:33 PM Channel
— SampleName; Fabrazyme Description NOT SEC purified
   Date Acquired 3/21/02 4:23:54 PM Channel

TREATMENT OF α-GALACTOSIDASE A DEFICIENCY

CROSS-REFERENCE TO RELATED APPLICATIONS

This application is a continuation of U.S. patent application Ser. No. 15/350,785, filed Nov. 11, 2016, which is a continuation of U.S. patent application Ser. No. 14/995,540, filed Jan. 14, 2016, now U.S. Pat. No. 9,523,113, which is continuation of U.S. patent application Ser. No. 12/761,287, filed Apr. 15, 2010, now U.S. Pat. No. 9,267,166, which is a continuation of U.S. patent application Ser. No. 11/403,618, filed Apr. 13, 2006, now U.S. Pat. No. 7,833,742, which is a divisional of U.S. patent application Ser. No. 10/423,225, filed Apr. 25, 2003, now abandoned, which claims benefit of U.S. Provisional Application No. 60/375,584, filed Apr. 25, 2002, the contents of which are incorporated herein by reference in their entirety.

FIELD OF THE INVENTION

This invention relates to improved α-galactosidase A compositions for the treatment of α-galactosidase A deficiencies including Fabry disease.

BACKGROUND OF THE INVENTION

Fabry disease is an X-linked inherited lysosomal storage disease characterized by severe renal impairment, angiokeratomas, and/or cardiovascular abnormalities, including ventricular enlargement and mitral valve insufficiency. Fabry disease also affects the peripheral nervous system, causing episodes of agonizing, burning pain in the extremities.

Fabry disease is caused by a deficiency in the enzyme α-galactosidase A (α-Gal A). The pathophysiology of Fabry Disease is well established: due to a lack of the lysosomal enzyme α-galactosidase A (α-Gal A), there is accumulation of globotriaosylceramide ($Gb_3$) throughout the body.

Due to the X-linked inheritance pattern of the disease, the majority of Fabry disease patients are male. Severely affected female heterozygotes are often observed, though female heterozygotes may become symptomatic later in life. A variant of Fabry disease correlates with left ventricular hypertrophy and cardiac disease. Nakano et al., New Engl. J Med. 333: 288-293 (1995). The cDNA and gene encoding human α-Gal A have been isolated and sequenced. Human α-Gal A is expressed as a 429-amino acid polypeptide, of which the N-terminal 31 amino acids are the signal peptide. The human enzyme has been expressed in Chinese Hamster Ovary (CHO) cells (Desnick et al., U.S. Pat. No. 5,356,804; Ioannou et al., J Cell Biol. 119: 1137 (1992)); insect cells (Calhoun et al., WO 90/11353); and human cells (Selden et al., U.S. Pat. Nos. 6,083,725 and 6,458,574B1). Enzyme replacement therapy is a currently used method of treatment for Fabry disease.

SUMMARY OF THE INVENTION

By understanding the pharmacokinetics and modification profile (e.g., carbohydrate, phosphate or sialylation modification) of human α-Gal A, we have developed novel pharmaceutical compositions of α-Gal A, kits for treatment of α-Gal A deficiency, methods of selecting an appropriate dose of α-Gal A for a patient, and methods of treating α-Gal A deficiency using such compositions. Also provided are methods of evaluating α-Gal A preparations, samples, batches, and the like, e.g., methods of quality control and determination of bioequivalence, e.g., with reference to the α-Gal A compositions described herein.

The α-Gal A dosing and administration strategies described herein reduce the amount and cost of α-Gal A required for α-Gal A replacement therapy and also reduce the required number of dose administrations.

Accordingly, in one aspect, the invention features a pharmaceutical composition that includes a human α-Galactosidase A (α-Gal A)) preparation. At doses below serum or plasma clearance saturation levels, serum clearance of the α-Gal A preparation from the circulation is preferably less than 4 mL/min/kg on the linear portion of the AUC vs. dose curve, more preferably less than about 3.5, 3, or 2.5 mL/min/kg, on the linear portion of the AUC vs. dose curve. The α-Gal A preparation can have an exponent "b" for the allometric scaling equation for clearance from circulation (serum or plasma) in mammals, $Y=a\,(BW)^b$, of at least 0.85, where Y is the clearance rate of α-Gal A (ml/min), "a" is a non-specific constant, and BW is body weight. The exponent "b" is preferably at least 0.88, more preferably at least 0.90, and most preferably at least 0.92 or at least 0.94.

In one embodiment, the α-Gal A is produced from human cells, e.g., primary human cells, e.g., primary human fibroblasts or a continuous human cell line. The cells and/or the α-Gal A preparation isolated from the cells can be modified to provide an α-Gal A preparation with desirable glycosylation, phosphorylation or sialylation characteristics.

In another embodiment, the α-Gal A is produced from non-human cells, e.g., CHO cells. The cells and/or the α-Gal A preparation isolated from the cells can be modified to provide an α-Gal A preparation with desirable glycosylation phosphorylation or sialylation characteristics.

In another aspect, the invention features a kit for the treatment of α-Gal A deficiency. The kit includes (a) a human α-Gal A glycoprotein preparation, where at doses below scrum or plasma clearance saturation levels, serum clearance of the α-Gal A preparation from the circulation is preferably less than 4 mL/min/kg on the linear portion of the area-under-the-curve (AUC) vs. dose curve, more preferably less than about 3.5, 3, or 2.5 mL/min/kg, on the linear portion of the AUC vs. dose curve, and (b) instructions to administer the preparation to a subject in need thereof.

The kit can also include instructions to administer a unit dose of the α-Gal A preparation of between about 0.05 mg and 2.0 mg per kilogram of body weight of the subject (mg/kg). In some embodiments, the kit includes instructions to administer a unit dose of the α-Gal A preparation of between 0.05 and 2.0 mg/kg, preferably between about 0.05 and 1.0 mg/kg, more preferably between about 0.05 and 0.5 mg/kg, e.g., and between 0.05 and less than 0.3 mg/kg. In one embodiment, the unit dose is less than 0.3 mg/kg. For example, the kit can include instructions to administer a unit dose of the α-Cal A preparation of about 0.1, 0.2, 0.3, 0.4, 0.5, 0.6, 0.7, 0.8, 0.9 or 1.0 mg per kilogram of body weight.

In other embodiments, the kit includes instructions to administer a unit dose of the x-Gal A preparation of between about $0.1 \times 10^6$ U/kg and $10 \times 10^6$ U/kg. In some embodiments, the kit includes instructions to administer a unit dose of the α-Gal A preparation of between $0.1 \times 10^6$ U/kg and $5 \times 10^6$ U/kg, preferably between about $0.1 \times 10^6$ U/kg and $3 \times 10^6$ U/kg. For example, the kit can include instructions to administer a unit dose of the α-Gal A preparation of about 0.1, 0.2, 0.3, 0.5, 1, 2, 3, 5 or up to $10 \times 10^6$ U/kg.

In some embodiments, the kit also includes instructions to administer the unit dose no more than once every 7 days. For example, the instructions can include instructions to administer the unit dose no more than once every 7 days, 10 days, 14 days, 21 days, 4 weeks, 6 weeks, 8 weeks or 10 weeks.

In another aspect, the invention features a kit for the treatment of α-Gal A deficiency. The kit includes a human α-Gal A glycoprotein preparation and one or more of the following instructions: (a) instructions to administer the preparation to a subject in need thereof at a unit dose of between 0.05 and 2.0 mg/kg, preferably between about 0.05 and 1.0 mg/kg, more preferably between about 0.05 and 0.5 mg/kg, e.g., between 0.05 and less than 0.3 mg/kg; (b) instructions to administer a unit dose of the α-Gal A preparation of between $0.1 \times 10^6$ U/kg and $10 \times 10^6$ U/kg, e.g., between $0.1 \times 10^6$ U/kg and $5 \times 10^6$ U/kg, preferably between about $0.1 \times 10^6$ U/kg and $3 \times 10^6$ U/kg; or (c) instructions to administer the preparation no more than about once every 8 weeks, 6 weeks, 4 weeks, 21 days, 14 days, 10 days, or 7 days.

The reagents of a kit described herein may be packaged in containers in predetermined amounts. A kit embodying features of the present invention, generally designated by the numeral 2, is illustrated in FIG. 16. Kit 2 is comprised of the following major elements: packaging 4, an α-Gal A preparation described herein 6, and instructions 8. Optionally, the kit may include an additional agent 10. The additional agent can be, e.g., a pharmaceutical buffer or solution, e.g., for dissolving or diluting the α-Gal A preparation 6. Instructions 8 can be, e.g., printed material on how to administer the preparation 6 and may include information on suitable dosage. Preferred instructions comprise instructions to administer the α-Gal A preparation 6 in a unit dose described herein. Packaging 4 is a box-like structure for holding a vial (or number of vials) containing an α-Gal A preparation of the invention 6, instructions 8, and, optionally, a vial (or number of vials) containing an agent 10. An individual skilled in the art can readily modify packaging 4 to suit individual needs.

The invention also features a method of selecting a unit dose range of α-Gal A for treatment of a subject having an α-Gal A deficiency. The method includes: providing the body weight of a subject, e.g., weighing the subject or obtaining the subject's body weight from the subject, from a health care provider of the subject, or from a database; and determining the value of the range between 0.05 mg and 2 mg (e.g., between 0.05 and 0.5 mg or between 0.05 and less than 0.3 mg) of α-Gal A per kilogram of body weight of the subject. The selected unit dose range can be used to select a regimen of α-Gal A replacement therapy for the subject. The method can also include evaluating the subject for one or more of: basal ax-Gal A levels, e.g., α-Gal A serum concentration; cardiovascular function; renal function; liver function, age, sex.

In a preferred embodiment, the unit dose saturates liver uptake of the α-Gal A by having $C_{max}$ (maximum serum concentration following drug infusion) greater than $2 \times 10^{-9}$ M.

In another aspect, the invention also features a method of treating a subject having or at risk for having α-Gal A deficiency. The method includes administering to a subject in need thereof a human α-Gal A glycoprotein preparation, where at doses below serum or plasma clearance saturation levels, serum clearance of the α-Gal A preparation following intravenous infusion from the circulation is preferably less than 4 mL/min/kg on the linear portion of the AUC vs. dose curve, more preferably less than about 3.5, 3, or 2.5 mL/min/kg, on the linear portion of the AUC vs. dose curve, e.g., a human α-Gal A glycoprotein preparation described herein above. As described elsewhere herein the unit dose administered preferably saturates liver uptake of the α-Gal A.

In a preferred embodiment, the preparation is administered intravenously, although it may be formulated for oral, subcutaneous, or intrathecal, administration, as described elsewhere herein.

In another aspect, the invention includes a method of treating a subject having or at risk for α-Gal A deficiency. The method includes one or more of (a)-(c): (a) administering to a subject in need thereof a human α-Gal A glycoprotein preparation at a unit dose of between about 0.05 and 2.0 mg per kilogram of body weight, preferably between 0.05 and 1.0 mg/kg or between 0.05 and 0.5 mg/kg, e.g., between 0.05 and less than 0.3 mg/kg, e.g., about 0.25, 0.20, 0.15 or 0.1 mg per kilogram of body weight of the subject; (b) administering to a subject in need thereof a human α-Gal A glycoprotein preparation at a unit dose of the α-Gal A preparation of between $0.1 \times 10^6$ U/kg and $10 \times 10^6$ U/kg, e.g., between $0.1 \times 10^6$ U/kg and $5 \times 10^6$ U/kg, preferably between about $0.1 \times 10^6$ U/kg and $3 \times 10^6$ U/kg; (c) administering to a subject in need thereof a human α-Gal A glycoprotein preparation no more than once every 7 days, e.g., no more than once every 10 days, 14 days, 21 days, 4 weeks, 6 weeks, or 8 weeks. In some embodiments, there are at least 7, 10, 14, 21, 30 or 60 days between each administration. In some embodiments, the preparation is administered over a period of at least 8, 16, 24, 36, 48, weeks or even longer, e.g., at least 1, 2, or 3 years.

In one embodiment, the human α-Gal A glycoprotein preparation is administered at least twice, preferably 3, 4, 5, 6 times or more, but no more than once every 7 days, preferably 10 days, more preferably 14 days or more, e.g., 21 days, 4 weeks, 6 weeks, 7 weeks, 8 weeks or more.

In a preferred embodiment, the unit dose saturates liver uptake of the α-Gal A, so as to allow administered α-Gal A to bypass the liver and be available to other tissues in the body.

In a preferred embodiment, the preparation is administered intravenously.

In another aspect, the invention features a unit dose of human α-Gal A described herein packaged in a container, e.g., a glass or plastic container or delivery device, e.g., a syringe. The unit dose is equivalent to between 0.05 and 2 mg/kg. e.g., between 0.05 and 1.0 mg/kg, preferably between 0.05 and 0.5 mg/kg, more preferably between 0.05 and less than 0.3 mg/kg of body weight of the subject for which it is intended. The activity of the α-Gal A preparation is generally between about 2.0 and $4.5 \times 10^6$ U/mg. For example, the container or delivery device can include between 2.0 and 32.0 mg of human α-Gal A described herein for an adult unit dose, e.g., the container or delivery device can include about 2, 4, 6, 8, 10, 12, 14, 16, 18, 20, 25 or 30 mg of α-Gal A for an adult dose.

Although not bound by any theory, it is believed that the α-Gal A preparations described herein can be predominantly cleared from the blood through mannose-6-phosphate (M6P) receptors. In preferred embodiments, less than 25%, 20%, 16%, 14% (as measured between 40 hours and 50 hours, e.g., approximately 44 hours, after dosing) or less of the α-Gal A preparation, e.g., a preparation described herein, is taken into the liver upon administration to a subject. At doses below serum or plasma clearance saturation levels, serum clearance of the α-Gal A preparation from the circulation is preferably less than 4 mL/min/kg on the linear portion of the AUC vs. dose curve, more preferably less than about 3.5, 3, or 2.5 mL/min/kg, on the linear portion of the AUC vs. dose curve. An α-Gal A preparation described herein exhibits a liver saturation curve as follows:

mg α-Gal A/liver=2.1 mg $(1-e^{Dose/4.7})$, where dose is the total dose (in mg) administered to a typical 75 kg patient. The coefficient of variation (CV) can be, e.g., about 0.40. (Doses and amounts would be adjusted accordingly for larger or smaller patients).

In some embodiments, the α-Gal A preparation of the compositions, methods and kits described herein is isolated from human cells genetically engineered to produce α-Gal A. In other embodiments, the α-Gal A preparation can be isolated from non-human cells (e.g., CHO cells), where the cell has been genetically engineered to produce α-Gal A. In some embodiments, one or more of: the α-Gal A expression construct, the human or non-human cells, or the α-Gal A isolated from the human or non-human cells can be modified to provide an α-Gal A preparation with altered glycosylation, e.g., altered glycan, sialylation or phosphate structures. For example, a non-human cell genetically engineered to produce a human α-Gal A (or the purified α-Gal A) can be modified to mimic the glycosylation characteristics of α-Gal A produced in human cells. In one embodiment, the cells can be modified, e.g., genetically engineered, to express one or more exogenous α-Gal A modifying enzyme, e.g., a glycosidase, glycosyl transferase, phosphoryl transferase, or sialyl transferase. In one embodiment, the α-Gal A coding sequence can be modified to have more or fewer (preferably more) glycosylation sites. In another embodiment, the cells can be exposed to one or more inhibitor or other modulator of glycosylation enzymes, e.g., kifunensine or swainsonine. In yet another embodiment, the α-Gal A, once isolated from the cells, can be modified, e.g., cleaved or chemically modified (e.g. by changing the number of moles of sialic acid and/or mannose-6-phosphate per mole of α-Gal A), e.g., with a phosphatase inhibitor, kinase, glycosidase, glycosyl transferase, phosphoryl transferase, or sialyl transferase.

In preferred embodiments, an α-Gal A preparation described herein is enriched in neutral, mono-sialylated and di-sialylated glycan structures (combined) relative to more highly sialylated structures such as tri-sialylated and tetra-sialylated structures. For example, a preferred α-Gal A preparation has one or more of: (a) at least about 22% neutral glycans, e.g., at least about 25% or 30% neutral glycans; (b) at least about 15%, 20%, or 25% mono-sialylated glycans; (c) at least about 35%, preferably at least about 40%, 45%, or 50% neutral and mono-sialylated glycans combined; (d) at least about 75%, 76%, 78% or more neutral, mono- and di-sialylated glycans combined; and (c) less than about 35%, preferably less than about 25%, 20%, 18% or about 15% tri- and tetra-sialylated glycan structures combined.

In preferred embodiments, an α-Gal A preparation described herein has, on average, more than one complex glycan per monomer, preferably at least 50% complex glycans per monomer, e.g., an average of 1.5 complex glycans or more per monomer.

In preferred embodiments, an α-Gal A preparation described herein has at least 5%, preferably at least 7%, 10% or 15% neutral glycans.

In preferred embodiments, an α-Gal A preparation described herein has less than 45% phosphorylated glycans. For example, the preparation has less than about 35%, 30%, 25%, or 20% phosphorylated glycans.

In preferred embodiments, an α-Gal A preparation described herein has a total proportion of sialylated glycans greater than about 45%, e.g., greater than 50% or 55%.

In a preferred embodiment, the ratio of sialic acid to mannose-6-phosphate in the α-Gal A preparation (on a mole per mole basis) is greater than 1.5 to 1, preferably greater than 2 to 1, more preferably greater than 3 to 1, most preferably greater than 3.5 to 1 or higher.

In one embodiment, the percent ratio of sialylated glycans to phosphorylated glycans is greater than 1, preferably greater than 1.5, more preferably greater than 2, e.g., greater than about 2.5 or 3.

The α-Gal A compositions and methods described herein are useful for treatment of individuals with α-Gal A deficiency. The α-Gal A compositions and methods described herein provide treatments that are cost effective and minimize the required dosage and frequency of administrations of α-Gal A.

In another aspect, the invention features various methods of evaluating, e.g., analyzing, selecting or classifying an α-Gal A preparation, sample, batch or other composition. The methods can be used to determine the structural and/or biological parameters (e.g., the carbohydrate composition, phosphate profile, sialylation profile, tissue distribution, or serum clearance characteristics) of the preparation or sample. By way of a non-limiting example, the methods are used to determine if the preparation or sample has one or more physical or functional property of an α-Gal A described herein. For example, one can compare a sample α-Gal A composition to a reference α-Gal A composition, e.g., a human α-Gal A composition described herein, e.g., a human α-Gal A having desirable pharmacokinetic or biological properties, such as a human α-Gal A prepared from human cells, e.g., human fibroblasts. The methods are useful, inter alia, for quality control and/or bioequivalence studies of α-Gal A preparations.

In one aspect, the method includes obtaining or providing a test α-Gal A preparation and determining if the preparation has at least one (preferably at least two, more preferably at least three or more, e.g., at least four, five, six or seven) of the following structural characteristics: (1) is enriched in neutral, mono-sialylated and di-sialylated glycan structures (combined) relative to more highly sialylated structures, for example, has (i) at least about 22% neutral glycans, e.g., at least about 25% or 30% neutral glycans, (ii) at least about 15%, 20%, or 25% mono-sialylated glycans. (iii) at least about 35%, preferably at least about 40%, 45%, or 50% neutral and mono-sialylated glycans combined, and/or (iv) at least about 75%, 76%, 78% or more neutral, mono- and di-sialylated glycans combined; (2) has less than about 35%, preferably less than about 25%, 20%, 18% or about 15% tri- and tetra-sialylated glycan structures combined; (3) has at least 50%, preferably at least 67% complex glycans; (4) has less than about 45% phosphorylated glycans, preferably less than about 35%, more preferably less than about 30%, 25% or 20% phosphorylated glycans; (5) has greater than about 45%, preferably greater than about 50 or 55% sialylated glycans; (6) has a ratio of sialic acid to mannose-6-phosphate on a mole per mole basis greater than 1.5 to 1, preferably greater than about 2 to 1, more preferably greater than about 3 to 1 or 3.5 to 1; and (7) has a ratio of sialylated glycans to phosphorylated glycans greater than 1, preferably greater than 1.5, more preferably greater than about 2, 2.5 or 3; and/or has one or more of the following biological or pharmacokinetic characteristics: (a) serum clearance from human circulation is less than 4 mL/min/kg on the linear portion of the AUC vs. close curve, more preferably less than about 3.5, 3, or 2.5 mL/min/kg, on the linear portion of the AUC vs. dose curve; (b) the preparation is preferentially targeted to capillary/vascular endothelial cells, renal glomerular epithelial cells (podocytes) and glomerular mesangial cells, renal endothelial cells, cardiac myocytes, liver endothelial cells, liver sinusoidal cells, pulmonary cells, and/or neural cells; and (c) is not taken up by liver hepatocytes.

A test preparation that has one or more of the aforementioned characteristics can be selected, classified, formulated, packaged, or passed on to other downstream processing. For example, such a preparation can be selected for a particular pharmaceutical use. The possession by the test preparation of one or more (preferably at least two, more preferably at least three or more, e.g., at least four, five, six or seven) of the aforementioned structural parameters (1)-(7) is positively correlated with (and can thus be used to predict) desirable pharmacokinetic parameters or biological activity, e.g., one or more of the biological or pharmacokinetic characteristics (a-(c). The correlation or predictive information can be used, e.g., to design an α-Gal A therapeutic preparation for a specific patient or a specific variant of Fabry disease (e.g., renal variant Fabry disease or cardiac variant Fabry disease). The correlation or prediction information can be recorded (e.g., in a print or computer readable medium).

In some embodiments, a biological activity or pharmacokinetic parameter of the test α-Gal A preparation or sample is predicted from its carbohydrate signature. In other embodiments, a biological activity or pharmacokinetic parameter of the preparation or sample is determined experimentally.

The result of the determination (which can be, e.g., a value for any of: the amount of neutral, mono-, di-, tri- or tetra-sialylated glycans or combinations thereof; the amount of complex glycans; the amount of phosphorylated glycans; the amount of sialylated glycans: the ratio of sialic acid to mannose-6-phosphate on a mole per mole basis, or the ratio of sialylated glycans to phosphorylated glycans), is preferably entered into a record, e.g., a print or computer-readable record, such as a laboratory record or dataset. The record can include other information, such as a specific sample identifier for the preparation, a dale, an operator of the method, or information about the enzymatic activity, source, method of purification or biological activity of the preparation. The record can be used to store or provide information about the test preparation. For example, the record can be used to provide information (e.g., to the government, a health care provider, insurance company or patient) related to the α-Gal A preparation or its use e.g., in the form of informational, marketing or instructional material, e.g., print material or computer readable material (e.g., a label). The record or information derived from the record can be used, e.g., to identify the test preparation as suitable or unsuitable for pharmaceutical or therapeutic use. For example, a test α-Gal A preparation determined to have one or more of the aforementioned structural parameters (1)-(7) can be identified as having desirable pharmacokinetic parameters or biological activity (e.g., the aforementioned parameters (a)-(c).

The methods described herein can also be used to compare batch-to-batch variation of an α-Gal A preparation. In this case, any of the structural or pharmacokinetic parameters described hereinabove can be evaluated for a plurality of α-Gal A batches, e.g., different batches made from the same purification protocol. In a preferred embodiment, the method includes selecting a batch with less than a preselected range of variation (e.g., less than 10%, preferably less than 5%, more preferably less than 2.5% or less variation) from one or more of the aforementioned structural or biological parameters (1)-(7) or (a)-(c). When multiple preparations are analyzed (e.g., different batches of an α-Gal A preparation), entering the result of the determinations into a record can include generating a dataset of the determinations. e.g., a print or computer-readable dataset. The dataset can include a correlation of a determined structural characteristic with a predicted or experimentally evaluated biological activity or pharmacokinetic parameter.

The α-Gal A sample to be tested can be derived from any cell, but preferably is derived from a mammalian cell, e.g., a human or non-human cell, such as a CHO cell. In some embodiments, the carbohydrate signature of the sample has been modified, e.g., by art-recognized methods, before the determination step is performed, e.g., by glycoengineering, e.g., as described herein, by treatment with a glycosidation enzyme such as a glycosyl transferase or glycosidase, or treatment of the cell or preparation with a phosphoryl transferase, sialyl transferase, phosphatase inhibitor, kinase, or inhibitor of glycosylation, or by co-expression in the cell (e.g., via co-transfection) of a DNA encoding any of the foregoing enzymes or other carbohydrate modifying enzymes.

The carbohydrate signature of the sample can be obtained by methods known in the art, e.g., by ion exchange chromatography, high performance anion exchange (HPAE) chromatography, high performance liquid chromatography (HPLC), or mass spectroscopy. Evaluating the carbohydrate signature can include evaluating the composition, charge, phosphorylation, and/or sialylation of the glycans of the preparation.

In another aspect, the invention features a method of producing a human α-Gal A preparation (e.g., an improved α-Gal A preparation). The method includes providing a human α-Gal A preparation harvested from a cell; and modifying the glycan structure of the α-Gal A preparation to match one or more (preferably at least two, more preferably at least three or more, e.g., at least four, five, six or seven) of the following parameters: (I) enrichment in neutral, mono-sialylated and di-sialylated glycan structures (combined) relative to more highly sialylated structures, for example, has (i) least about 22% neutral glycans, e.g., at least about 25% or 30% neutral glycans, (ii) at least about 15%, 20%, or 25% mono-sialylated glycans, (iii) at least about 35%, preferably at least about 40%, 45%, or 50% neutral and mono-sialylated glycans combined, and/or (iv) at least about 75%, 76%, 78% or more neutral, mono- and di-sialylated glycans combined; (2) less than about 35%, preferably less than about 25%, 20%, 18% or about 15% tri- and tetra-sialylated glycan structures combined; (3) at least 50%, preferably at least 67% complex glycans; (4) less than about 45% phosphorylated glycans, preferably less than about 35%, more preferably less than about 30%, 25% or 20% phosphorylated glycans; (5) greater than about 45%, preferably greater than about 50 or 55% sialylated glycans; (6) a ratio of sialic acid to mannose-6-phosphate on a mole per mole basis greater than 1.5 to 1, preferably greater than about 2 to 1, more preferably greater than about 3 to 1 or 3.5 to 1; and (7) a ratio of sialylated glycans to phosphorylated glycans greater than 1, preferably greater than 1.5, more preferably greater than about 2, 2.5 or 3. The glycan structure can be modified by methods known in the art, e.g., by glycoengineering (e.g., by genetically engineering the cell to produce a human α-Gal A having a non-naturally occurring glycosylation site; and/or genetically engineering the cell to produce a glucosidase, glycosyl transferase, phosphoryl transferase, phosphatase, or sialyl transferase); by selective isolation of glycoforms during the α-Gal A purification process; by treatment of the cell or preparation with a carbohydrate modifying enzyme; or treatment of the cell or preparation with an inhibitor of glycosylation, e.g., kifunensine, and/or by co-expression in the cell (e.g., via co-transfection) of a DNA encoding any of the foregoing enzymes or other carbohydrate modifying enzymes.

In a preferred embodiment, the method includes the step of analyzing (e.g., assaying) one or more parameters of the carbohydrate signature, biological activity or pharmacokinetic parameter of the α-Gal A preparation after modification.

The invention also features a method of treating a subject, e.g., a human. The method includes: providing or obtaining a panel of two or more α-Gal A preparations having different glycan characteristics; and selecting an α-Gal A preparation having a carbohydrate signature that matches one or more (preferably at least two, more preferably at least three or more, e.g., at least four, five, six or seven) of the aforementioned parameters (1)-(7) and/or (a)-(c) for treating the subject.

The method can also include administering one or more doses of a therapeutically effective amount of the selected α-Gal A preparation to the subject. The subject can be evaluated before, during, and/or after the administration. For example, the tissue distribution or serum clearance of the α-Gal A preparation can be evaluated in the subject, e.g., evaluated repeatedly over time. The dose of the preparation can then be adjusted according to the result of the evaluation. The subject can also be evaluated or monitored for status. e.g., clinical status, in response to the administration of the α-Gal A preparation.

Different carbohydrate signatures, e.g., each parameter (1) to (7) or different combinations of parameters (1)-(7) can be correlated with having desirable pharmacokinetic or other biological properties for different populations, e.g., populations that differ by stage or type of disease (e.g., cardiac vs. renal type Fabry disease), age, gender, ethnic background, or genotype.

By "α-Gal A deficiency," it is meant any deficiency in the amount or activity of this enzyme in a patient, resulting in abnormal accumulations of neutral glycolipids (e.g., globotriaosylceramide) primarily in capillary endothelial cells, renal glomerular epithelial cells (podocytes) and glomerular mesangial cells, and/or cardiac myocytes. The deposits of this material can result in severe neuropathic pain (e.g., acroparasthesia and lacerative pain), serious renal and cardiovascular disease, and/or stroke. The glycolipid accumulation may induce severe symptoms as typically observed in males who are suffering from Fabry disease. Alternatively, the accumulation may induce relatively mild symptoms, as can sometimes be seen in some heterozygous female carriers of the defective gene. Affected individuals have a greatly shortened life expectancy; death usually results from renal, cardiac, and/or cerebrovascular complications at approximately the fourth and fifth decade in life.

A "carbohydrate signature" of an α-Gal A preparation is one or more identifying characteristic of the glycan structure of a given preparation or sample of α-Gal A. The carbohydrate signature can be qualitative or quantitative. For example, a carbohydrate signature of an α-Gal A preparation can include one or more of the following identifying characteristics: (a) the relative level, percentage range or specific value of complex vs. high mannose or hybrid glycans; (b) the relative level, percentage range or specific value of neutral and sialylated, e.g., mono-sialylated, di-sialylated, tri-sialylated and tetra-sialylated glycan structure; (c) the relative level, percentage range or specific value of phosphorylated or non-phosphorylated glycans; (d) the relative level, percentage range or specific value of sialylated glycans; (e) the relative or specific charge profile of the glycans of the preparation; (f) the relative or specific ratio of one type of charged monosaccharide to another, e.g., the ratio of sialic acid to mannose-6-phosphate; or the ratio of sialylated glycans to phosphorylated glycans.

BRIEF DESCRIPTION OF THE DRAWINGS

FIG. 1 is a representation of the sequence of α-Gal A cDNA, including the sequence that encodes the signal peptide (SEQ ID NO: 1).

FIG. 2 is a representation of the human α-Gal A amino acid sequence (SEQ ID NO:2).

DETAILED DESCRIPTION OF THE INVENTION

Introduction

Figure 3A:
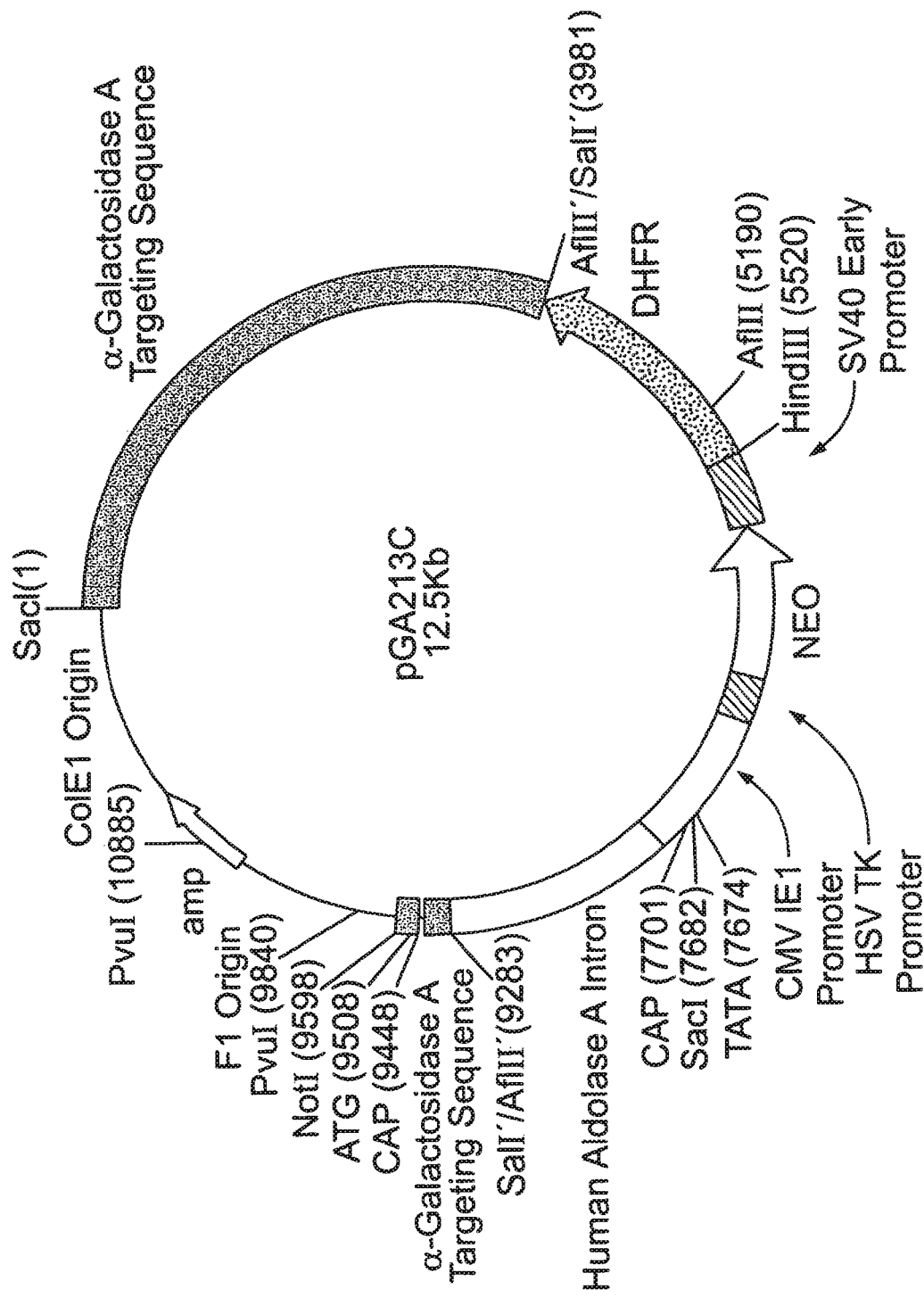
FIG. 3A is a schematic map of pGA213C.

It has been discovered that human α-Gal A can be made having modifications (e.g., in carbohydrate structure, e.g., glycan, phosphate or sialylation modifications) that result in a human α-Gal A preparation having pharmacokinetic properties that are desirable for enzyme replacement therapy for α-Gal A deficiency. For example, a preparation of human α-Gal A produced from human cells genetically engineered to produce human α-Gal A has an exponent "b" for the allometric scaling equation for clearance from the circulation in humans, $Y=a(BW)^b$, of at least 0.85 (preferably up to 0.92), where Y is clearance rate of α-Gal A (ml/min), "a" is a non-specific constant, and 1W is body weight. Such an α-Gal A preparation, as described herein, can be predominantly taken up by M6P receptors and has a serum clearance less rapid than that of human α-Gal A produced in non-human cells, e.g., CHO cells. Accordingly, pharmaceutical compositions and kits for treatment of α-Gal A deficiency described herein include such a α-Gal A preparations that are administered in a unit dose substantially smaller than what is currently used in the art. For example, in some embodiments, the α-Gal A preparations described herein are administered in a unit dose of between 0.05 mg and 2.0 mg per kilogram of body weight (mg/kg), preferably between 0.05 and 5 mg/kg, more preferably between 0.05 and 0.3 mg/kg (e.g., about 0.1, 0.2, 0.25, 0.3, 0.4 or 0.5 mg/kg). The unit dose can be, e.g., between $0.1\times10^6$ U/kg and $10\times10^6$ U/kg. In some embodiments, the unit dose of the α-Gal A preparation is between $0.1\times10^6$ U/kg and $5\times10^6$ U/kg, preferably between about $0.1\times10^6$ U/kg and $3\times10^6$ U/kg. In other embodiments, the α-Gal A preparations described herein are administered no more than once every 7 days, e.g., once every 10 days, 14 days or 21 days, or once every 4, 5, 6, 7 or 8 weeks. For some patients, even less frequent dosing may be possible, e.g., once every 9, 10, 11, 12 weeks or more.

It is believed that the desirable pharmacokinetics result at least in part from the glycosylation patterns of the α-Gal A preparation. The glycosylation patterns required for the desirable pharmacokinetics of human α-Gal A (e.g., at least 50% complex glycans per α-Gal A monomer, on average; a ratio of sialic acid to mannose-6-phosphate (on a mole per mole basis) greater than 1.5 to 1, preferably greater than 2 to 1, more preferably greater than 3 to 1, most preferably greater than 3.5 to 1 or higher) can be achieved through a number of methods known in the art. Certain representative embodiments are summarized and described in greater detail below.

The α-Gal A preparations described herein can be produced in any cell (an α-Gal A production cell) for the treatment of Fabry disease. In some embodiments, the compositions and methods described herein use human α-Gal A produced using standard genetic engineering techniques (based on introduction of the cloned α-Gal A gene or cDNA into a host cell), or gene activation, described in more detail below. The human α-Gal A can be produced in human cells, which provide the carbohydrate modifications that are important for the enzyme's pharmacokinetic activity.

However, human α-Gal A can also be produced in non-human cells, e.g., CHO cells. If the α-Gal A is produced in non-human cells, one or more of: the α-Gal A expression construct, the non-human cells, or the α-Gal A isolated from the non-human cells can be modified, e.g., as described herein below, to provide α-Gal A preparations having a glycosylation profile that results in desirable pharmacokinetic properties.

Cells Suitable for Production of Human α-Gal A

Purified human α-Gal A can be obtained from cultured cells, preferably genetically modified cells, e.g., genetically modified human cells or other mammalian cells, e.g., CHO cells. Insect cells can also be used.

When cells are to be genetically modified for the purposes of treatment of Fabry disease, the cells may be modified by conventional genetic engineering methods or by gene activation.

According to conventional methods, a DNA molecule that contains an α-Gal A cDNA or genomic DNA sequence may be contained within an expression construct and transfected into primary, secondary, or immortalized cells by standard methods including, but not limited to, liposome-, polybrene-, or DEAE dextran-mediated transfection, electroporation, calcium phosphate precipitation, microinjection, or velocity driven microprojectiles (see, e.g., U.S. Pat. No. 6,048,729, incorporated herein by reference).

Alternatively, one can use a system that delivers the genetic information by viral vector. Viruses known to be useful for gene transfer include adenoviruses, adeno associated virus, herpes virus, mumps virus, pollovirus, retroviruses, Sindbis virus, and vaccinia virus such as canary pox virus.

Alternatively, the cells may be modified using a gene activation ("GA") approach, for example, as described in U.S. Pat. Nos. 5,641,670; 5,733,761; 5,968,502; 6,200,778; 6,214,622; 6,063,630; 6,187,305; 6,270,989; and 6,242,218, each incorporated herein by reference. α-Gal A made by gene activation is referred to herein as GA-GAL (Selden et al., U.S. Pat. Nos. 6,083,725 and 6,458,574B1).

Accordingly, the term "genetically modified," as used herein in reference to cells, is meant to encompass cells that express a particular gene product following introduction of a DNA molecule encoding the gene product and/or including regulatory elements that control expression of a coding sequence for the gene product. The DNA molecule may be introduced by gene targeting or homologous recombination, i.e., introduction of the DNA molecule at a particular genomic site. Homologous recombination may be used to replace the defective gene itself (the defective α-Gal A gene or a portion of it could be replaced in a Fabry disease patient's own cells with the whole gene or a portion thereof).

As used herein, the term "primary cell" includes cells present in a suspension of cells isolated from a vertebrate tissue source (prior to their being plated, i. e., attached to a tissue culture substrate such as a dish or flask), cells present in an explant derived from tissue, both of the previous types of cells plated for the first time, and cell suspensions derived from these plated cells.

"Secondary cells" refers to cells at all subsequent steps in culturing. That is, the first Lime a plated primary cell is removed from the culture substrate and replated (passaged), it is referrcd to as a secondary cell, as are all cells in subsequent passages.

A "cell strain" consists of secondary cells which have been passaged one or more tilmes; exhibit a finite number of mean population doublings in culture; exhibit the properties of contact-inhibited, anchorage dependent growth (except for cells propagated in suspension culture); and are not immortalized.

By "immortalized cell" or "continuous cell line" is meant a cell from an established cell line that exhibits an apparently unlimited lifespan in culture.

Examples of primary or secondary cells include fibroblasts, epithelial cells including mammary and intestinal epithelial cells, endothelial cells, formed elements of the blood including lymphocytes and bone marrow cells, glial cells, hepatocytes, keratinocytes, muscle cells, neural cells, or the precursors of these cell types. Examples of immortalized human cell lines useful in the present methods include, but are not limited to, Bowes Melanoma cells (ATCC Accession No. CRL 9607), Daudi cells (ATCC Accession No. CCL 213), HeLa cells and derivatives of HeLa cells (ATCC Accession Nos. CCL 2, CCL 2.1, and CCL 2.2), HL-60 cells (ATCC Accession No. CCL 240), HT-1080 cells (ATCC Accession No. CCL 121), Jurkat cells (ATCC Accession No. TIB 152), KB carcinoma cells (ATCC Accession No. CCL 17), K-562 leukemia cells (ATCC Accession No. CCL 243), MCF-7 breast cancer cells (ATCC Accession No. BTH 22), MOLT-4 cells (ATCC Accession No. 1582), Namalwa cells (ATCC Accession No. CRL 1432). Raji cells (ATCC Accession No. CCL 86), RPMI 8226 cells (ATCC Accession No. CCL 155), U-937 cells (ATCC Accession No. CRL 15 93), WI-3 8VAI 3 sub line 2R4 cells (ATCC Accession No. CLL 75. 1), CCRF-CEM cells (ATCC Accession No. CCL 119), and 2780AD ovarian carcinoma cells (Van der Blick et al., Cancer Res. 48: 5927-5932, 1988), as well as heterohybridoma cells produced by fusion of human cells and cells of another species.

Following the genetic modification of human cells to produce a cell which secretes α-Gal A, a clonal cell strain consisting essentially of a plurality of genetically identical cultured primary human cells or, where the cells are immortalized, a clonal cell line consisting essentially of a plurality of genetically identical immortalized human cells, may be generated. In one embodiment, the cells of the clonal cell strain or clonal cell line are fibroblasts. In a preferred embodiment the cells are secondary human fibroblasts, e.g., BRS-11 cells. Example 1 provides additional guidance on the production of cells genetically engineered to produce human α-Gal A.

After genetic modification, the cells are cultured under conditions permitting production and secretion of α-Gal A. The protein is isolated from the cultured cells by collecting the medium in which the cells are grown, and/or lysing the cells to release their contents, and then applying protein purification techniques.

Increasing Circulatory Half Life, Cellular Uptake and/or Targeting of α-Gal A to Appropriate Tissues The data described herein shows that human α-Gal A can be made having modifications (e.g., carbohydrate, phosphate or sialylation modifications) that result in pharmacokinetic properties of the enzyme that are desirable for use in enzyme replacement therapy for α-Gal A deficiency. One method of making such human α-Gal A preparations is to produce human α-Gal A from human cells.

There are differences in the glycosylation characteristics of human and non-human cells (e.g., CHO cells) such that the production of α-Gal A (or indeed, of any glycoprotein) from human cells necessarily results in a structurally different protein than that produced in CHO cells. Although not bound by theory, these differences are thought to be important for the desirable pharmacokinetics of human α-Gal A preparations in the compositions and methods described herein. However, α-Gal A preparations described herein can also be produced from non-human cells, wherein either the cells, the α-Gal A coding sequence and/or the purified α-Gal A are modified. For example, non-human cells whose glycosylation machinery differs from human (e.g., CHO cells) can be genetically modified to express an enzyme of carbohydrate metabolism, e.g., α-2,6-sialyltransferase, that is present in human but not in CHO cells.

In another example, the cells can be genetically engineered to express an α-Gal A protein that has one or more modified glycosylation sites, e.g., a human or non-human cell can be genetically engineered to express an α-Gal A coding sequence in which one or more additional N-linked glycosylation sites have been added or deleted. The additional glycosylation sites can be glycosylated by the cellular machinery in the cell, e.g., the CHO cell, in which the modified α-Gal A coding sequence is expressed, thus providing an α-Gal A preparation that has an increased circulatory half-life, cellular uptake, and/or improved targeting to heart, kidney or other appropriate tissues compared to the unmodified α-Gal A, e.g., when expressed in non-human cells.

α-Gal A can also be modified (e.g., after isolation from a genetically engineered non-human cell) to resemble human α-Gal A produced in human cells. For example, a human α-Gal A preparation isolated from a non-human cell can be modified, e.g., phosphorylated or cleaved (e.g., with neuraminidase or phosphatase) before administration to a subject.

The circulating half-life, cellular uptake and/or tissue targeting can also be modified, inter alia, by (i) modulating the phosphorylation of α-Gal A; (ii) modulating the sialic acid content of α-Gal A; and/or (iii) sequential removal of the sialic acid and terminal galactose residues, or removal of terminal galactose residues, on the oligosaccharide chains on α-Gal A. Altered sialylation of α-Gal A preparations can enhance the circulatory half-life, cellular uptake and/or tissue targeting of exogenous α-Gal A. A change in the ratio of moles of mannose-6-phosphate per mole of sialic acid per molecule of α-Gal A can also result in improved cellular uptake, relative to that of hepatocytes, in non-hepatocytes such as liver endothelial cells, liver sinusoidal cells, capillary/vascular endothelial cells, renal glomerular epithelial cells (podocytes) and glomerular mesangial cells, renal endothelial cells, pulmonary cells, renal cells, neural cells, and/or cardiac myocytes. For example, a preferred ratio of sialic acid to mannose-6-phosphate in the α-Gal A preparation (on a mole per mole basis) is greater than 1.5 to 1, preferably greater than 2 to 1, more preferably greater than 3 to 1, most preferably greater than 3.5 to 1 or higher.

Glycan Remodeling

Glycoprotein modification (e.g., when α-Gal A is produced in non-human cells) can increase uptake of the enzyme in specific tissues other than liver and macrophages, e.g., increase uptake in capillary/vascular endothelial cells, renal glomerular epithelial cells (podocytes) and glomerular mesangial cells, renal endothelial cells, pulmonary cells, renal cells, neural cells, and/or cardiac myocytes. Using glycoprotein modification methods, human glycosylated α-Gal A preparations can be obtained, wherein between 35% and 85% of the oligosaccharides, preferably at least 50%, are charged.

Protein N-glycosylation functions by modifying appropriate asparagine residues of proteins with oligosaccharide structures, thus influencing their properties and bioactivities (Kukuruzinska & Lennon, Crit. Rev. Oral. Biol. Med. 9: 415-48 (1998)). An α-Gal A preparation described herein can have a high percentage of the oligosaccharides being negatively charged, primarily by the addition of one to four sialic acid residues on complex glycans, or of one to two phosphate moieties on high-mannose glycans, or of a single phosphate and a single sialic acid on hybrid glycans. Smaller amounts of sulfated complex glycans may also hbe present. A high proportion of charged structures serves two main functions. First, capping of penultimate galactose residues by 2,3- or 2,6-linked sialic acid prevents premature removal from the circulation by the asialoglycoprotein receptor present on hepatocytes. This receptor recognizes glycoproteins with terminal galactose residues.

Modifying the glycosylation pattern of α-Gal A produced in non-human cells to, e.g., resemble the pattern produced in human cells, gives important target organs such as heart and kidney the opportunity to endocytose greater amounts of enzyme from the plasma following enzyme infusion. Second, the presence of Man-6-phosphate on high-mannose or hybrid glycans provides an opportunity for receptor-mediated uptake by the cation-independent Man-6-phosphate receptor (CI-MPR). This receptor-mediated uptake occurs on the surface of many cells, including vascular endothelial cells, which are a major storage site of $Gb_3$ in Fabry patients. Enzyme molecules with two Man-6-phosphate residues have a much greater affinity for the CI-MPR than those with a single Man-6-phosphate.

The complexity of N-glycosylation is augmented by the fact that different asparagine residues within the same polypeptide may be modified with different oligosaccharide structures, and various proteins are distinguished from one another by the characteristics of their carbohydrate moieties.

Several approaches are provided herein for carbohydrate remodeling on a protein containing N-linked glycan chains. First, one can genetically engineer a cell, e.g., a non-human cell, to produce a human α-Gal A having a non-naturally occurring glycosylation site, e.g., one can engineer a human α-Gal A coding sequence to produce an α-Gal A protein having one or more additional glycosylation sites. The additional glycosylation sites can be glycosylated (e.g., with complex glycans) by the cellular machinery in the cell, e.g., the CHO cell, in which the modified α-Gal A coding sequence is expressed, thus providing an α-Gal A preparation that has improved circulatory half-life, cellular uptake and/or tissue targeting compared to the unmodified α-Gal A, e.g., when expressed in non-human cells.

Second, the proportion of charged α-Gal A can be increased by selective isolation of glycoforms during the purification process. The present invention provides for increasing the proportion of highly charged and higher molecular weight α-Gal A glycoforms by fractionation of α-Gal A species on chromatography column resins during and/or after the purification process. The more highly charged glycoform species of α-Gal A contain more sialic acid and/or more phosphate, and the higher molecular weight glycoforms would also contain the fully glycosylated, most highly branched and highly charged species. Selection of the charged species, or removal of the non-glycosylated, poorly glycosylated or poorly sialylated and/or phosphorylated α-Gal A species would result in a population of α-Gal A glycoforms with more sialic acid and/or a more desirable sialic acid to phosphate ratio in the preparation, therefore providing an α-Gal A preparation with better half-life, cellular uptake and/or tissue targeting, thereby having better therapeutic efficiency.

This fractionation process can occur on, but is not limited to, suitable chromatographic column resins utilized to purify or isolate α-Gal A. For example, fractionation can occur on, but is not limited to, cation exchange resins (such as SP-SepharoseG), anion exchange resins (Q-SepharoseG), affinity resins (Heparin Sepharose-b, lectin columns) size exclusion columns (Superdex 200) and hydrophobic interaction columns (Butyl Sepharose) and other chromatographic column resins known in the art.

Since α-Gal A is produced in cells as a heterogeneous mixture of glycoforms which differ in molecular weight and charge, α-Gal A tends to elute in relatively broad peaks from the chromatography resins. Within those elutions, the glycoforms are distributed in a particular manner depending on the nature of the resin being utilized. For example, on size exclusion chromatography, the largest glycoforms will tend to elute earlier on the elution profile than the smaller glycoforms. On ion exchange chromatography, the most negatively charged glycoforms will tend to bind to a positively charged resin (such as Q-Sepharoseg) with higher affinity than the less negatively charged glycoforms, and will therefore tend to elute later in the elution profile. In contrast, these highly negatively charged glycoforms may hind less lightly to a negatively charged resin, such as SP Sepharose8, than less negatively charges species, or may not even bind at all.

Fractionation and selection of highly charged and/or higher molecular weight glycoforms of α-Gal A can be performed on any α-Gal A preparation, such as that derived from genetically modified cells such as cells, e.g., human or non-human cells, modified by conventional genetic engineering methods or by gene activation (GA). It can be performed on cell lines grown in optimized systems to provide altered sialylation and phosphorylation as described herein, e.g., to provide a preparation with a ratio of sialic acid to mannose-6-phosphate (on a mole per mole basis) is greater than 1.5 to 1, preferably greater than 2 to 1, more preferably greater than 3 to 1, most preferably greater than 3.5 to 1 or higher.

A third approach for carbohydrate remodeling can involve modifying certain glycoforms on the purified α-Gal A by attachment of an additional terminal sugar residue using a purl lied glycosyl transferase and the appropriate nucleotide sugar donor. This treatment affects only those glycoforms that have an appropriate free terminal sugar residue to act as an acceptor for the glycosyl transferase being used. For example, α 2,6-sialyltransferase adds sialic acid in an α-2, 6-linkage onto a terminal Galβ1,4GlcNAc-R acceptor, using CMP-sialic acid as the nucleotide sugar donor. Commercially available enzymes and their species of origin include: fucose α 1,3 transferases III, V and VI (humans); galactose α 1,3 transferase (porcine); galactose β 1,4 transferase (bovine); mannose α 1,2 transferase (yeast); sialic acid α 2,3 transferase (rat); and sialic acid α 2,6 transferase (rat). After the reaction is completed, the glycosyl transferase can be removed from the reaction mixture by a glycosyl transferase specific affinity column consisting of the appropriate nucleotide bonded to a gel through a 6 carbon spacer by a pyrophosphate (GDP, UDP) or phosphate (CMP) linkage or by other chromatographic methods known in the art. Of the glycosyl transferases listed above, the sialyl transferases is particularly useful for modification of enzymes, such as α-Gal A, for enzyme replacement therapy in human patients. Use of either sialyl transferase with CMP-5-fluoresceinyl-neuraminic acid as the nucleotide sugar donor yields a fluorescently labeled glycoprotein whose uptake and tissue localization can be readily monitored.

A fourth approach for carbohydrate remodeling involves glyco-engineering, e.g., introduction of genes that affect glycosylation mechanisms of the cell, of the α-Gal A production cell to modify post-translational processing in the Golgi apparatus is a preferred approach.

A fifth approach for carbohydrate remodeling involves treating α-Gal A with appropriate glycosidases to reduce the number of different glycoforms present. For example, sequential treatment of complex glycan chains with neuraminidase, β-galactosidase, and β-hexosaminidase cleaves the oligosaccharide to the trimannose core.

A sixth approach for glycan remodeling involves the use of inhibitors of glycosylation, e.g., kifunensine (an inhibitor of mannosidase 1), swainsonine, or the like. Such inhibitors can be added to the cultured cells expressing a human α-Gal A. The inhibitors are taken up into the cells and inhibit glycosylation enzymes, such as glycosyl transferases and glycosidases, providing α-Gal A molecules with altered sugar structures. Alternatively, a cell genetically engineered to produce human α-Gal A can be transfected with glycosylation enzymes such as glycosyl transferases and glycosidases.

A seventh approach involves using glycosylation enzymes (e.g., glycosyl transferases or glycosidases) to remodel the carbohydrate structures in vitro, e.g., on an α-Gal A that has been isolated from a genetically engineered cell, as described herein.

Other approaches for glycan remodeling are known in the art.

Altering Half Life and/or Cellular Uptake of α-Gal A by Altering Sialylation

Sialylation affects the circulatory half-life and biodistribution of proteins. Proteins with minimal or no sialic acid are readily internalized by the asialoglycoprotein receptor (Ashwell receptor) on hepatocytes by exposed galactose residues on the protein. The circulating half-life of galactose-terminated α-Gal A can be altered by sequentially (1) removing sialic acid by contacting α-Gal A with neuraminidase (sialidase), thereby leaving the terminal galactose moieties exposed, and (2) removing the terminal galactoside residues by contacting the desialylated α-Gal A with β-galactosidase. The resulting α-Gal A preparation has a reduced number of terminal sialic acid and/or terminal galactoside residues on the oligosaccharide chains compared to α-Gal A preparations not sequentially contacted with neuraminidase and β-galactosidase. Alternatively, the circulating half-life of galactose-terminated α-Gal A can be enhanced by only removing the terminal galactoside residues by contacting the desialylated α-Gal A with β-galactosidase. The resulting α-Gal A preparation has a reduced number of terminal galactoside residues on the oligosaccharide chains compared to α-Gal A preparations not contacted with β-galactosidase. In a preferred embodiment, following sequential contact with neuraminidase and β-galactosidase, the resulting α-Gal A preparations are subsequently contacted with β-hexosaminidase, thereby cleaving the oligosaccharide to the trimannose core.

The sialic acid content of α-Gal A preparations can be increased by (i) isolation of the highly charged and/or higher molecular weight α-Gal A glycoforms during or after the purification process; (ii) adding sialic acid residues using cells genetically modified (either by conventional genetic engineering methods or gene activation) to express a sialyl transferase gene or cDNA; or (iii) fermentation or growth of cells expressing the enzyme in a low ammonium environment.

Altering Half Life and/or Cellular Uptake by Altering Phosphorylation

Altering the phosphorylation of an α-Gal A preparation described heroin can alter the circulatory half life and cellular uptake of the preparation into desired tissues. In preferred embodiments, an α-Gal A preparation has less than 45% phosphorylated glycans. For example, the preparation has less than about 35%, 30%, 25%, or 20% phosphorylated glycans. A desirable ratio of sialic acid:mannose-6-phosphate in the α-Gal A preparation (on a mole per mole basis) is a ratio greater than 1.5 to 1, preferably greater than 2 to 1, more preferably greater than 3 to 1, most preferably greater than 3.5 to 1 or higher.

The phosphorylation of α-Gal A preparations can be modified, e.g., increased or decreased, by (i) adding or removing phosphate residues using cells genetically modified (either by conventional genetic engineering methods or gene activation) to express a phosphoryl transferase or phosphatase gene or cDNA; (it) adding phosphatases, kinases, or their inhibitors to the cultured cells; or (iii) adding phosphatases, kinases, or their inhibitors to a purified α-Gal A preparation produced from a genetically engineered cell as described herein.

The concerted actions of two membrane-bound Golgi enzymes are needed to generate a Man-6-phosphate recognition marker on a lysosomal proenzyme. The first, UDP-N-acetylglucosamine: glycoprotein N-acetylglucosamine-1-phosphotransferase (GlcNAc phosphotransferase), requires a protein recognition determinant on lysosomal enzymes that consists of two lysine residues 34 Å apart and in the correct spatial relationship to a high mannose chain. The second, N-acetylglucosamine-1-phosphodiester α-N-acetyl-glucosaminidase (phosphodiester α-GlcNAcase), hydrolyzes the α-GlcNAc-phosphate bond exposing the Man-6-phosphate recognition site. These enzymes can be induced or inhibited by methods known in the art to provide an α-Gal A preparation with desirable phosphorylation characteristics (e.g., with a desirable ration of sialylated to phosphorylated glycans).

In one embodiment, an α-Gal A preparation with altered phosphorylation is obtained by first introducing into an α-Gal A production cell a polynucleotide which encodes for phosphoryl transferase, or by introducing a regulatory sequence by homologous recombination that regulates expression of an endogenous phosphoryl transferase gene. The α-Gal A production cell is then cultured under culture conditions which results in expression of α-Gal A and phosphoryl transferase. The α-Gal A preparation with increased phosphorylation compared to the α-Gal A produced in a cell without the polynucleotide is then isolated.

In still another embodiment, a glycosylated α-Gal A preparation with altered phosphorylation is obtained by adding a phosphatase inhibitor. e.g., bromotetramisole, or a kinase inhibitor, to cultured cells.

Using the methods described herein, α-Gal A preparations are obtained wherein at doses below serum or plasma clearance saturation levels, serum clearance of the α-Gal A preparation from the circulation is preferably less than 4 mL/min/kg on the linear portion of the AUC vs. dose curve, more preferably less than about 3.5, 3, or 2.5 mL/min/kg, on the linear portion of the AUC vs. dose curve. The α-Gal A preparation has an exponent "b" for the allometric scaling equation for clearance from the circulation in mammals, $Y=(BW)^b$, of at least 0.85, where Y is clearance of α-Gal A from the circulation (ml/min), "a" is a non-specific constant and BW is body weight. The exponent "b" is preferably at least 0.88, more preferably at least 0.90, and most preferably at least 0.92, 0.94 or higher.

In preferred embodiments, an α-Gal A preparation described herein is enriched in neutral, mono-sialylated and di-sialylated glycan structures (combined) relative to more highly sialylated structures such as tri-sialylated and tetra-sialylated structures. For example, a preferred α-Gal A preparation has one or more of: (a) at least about 22% neutral glycans, e.g., at least about 25% or 30% neutral glycans; (b) at least about 15%, 20%, or 25% mono-sialylated glycans; (c) at least about 35%, preferably at least about 40%, 45%, or 50% neutral and mono-sialylated glycans combined; (d) at least about 75%, 76%, 78% or more neutral, mono- and di-sialylated glycans combined; and (e) less than about 35%, preferably less than about 25%, 20%, 18% or about 15% tri- and tetra-sialylated glycan structures combined.

In preferred embodiments, an α-Gal A preparation described herein has, on average, more than one complex glycan per monomer, preferably at least 50% complex glycans per monomer, e.g., 2 complex glycans or more per monomer.

In preferred embodiments, an α-Gal A preparation described herein has at least 5%, preferably at least 7%, 10% or 15% neutral glycans.

In preferred embodiments, an α-Gal A preparation described herein has less than 45% phosphorylated glycans. For example, the preparation has less than about 35%, 30%, 25%, or 20% phosphorylated glycans.

In preferred embodiments, an the α-Gal A preparation described herein has a total proportion of sialylated glycans greater than about 45%, e.g., greater than 50% or 55%.

In a preferred embodiment, the ratio of sialic acid to mannose-6-phosphate in the α-Gal A preparation (on a mole per mole basis) is greater than 1.5 to 1, preferably greater than 2 to 1, more preferably greater than 3 to 1, most preferably greater than 3.5 to 1 or higher.

In one embodiment, the percent ratio of sialylated glycans to phosphorylated glycans is greater than 1, preferably greater than 1.5, more preferably greater than 2, e.g., greater than about 2.5 or 3.

PEGylation in other embodiments, the circulatory half-life of a human α-Gal A preparation is enhanced by complexing α-Gal A with polyethylene glycol (PEG). In a preferred embodiment, the α-Gal A preparation is complexed using tresyl monomethoxy PEG (TMPEG) to form a PEGylated-α-Gal A. The PEGylated-α-Gal A is then purified to provide an isolated, PEGylated-α-Gal A preparation. PEGylation of α-Gal A increases the circulating half-life, cellular uptake and/or tissue distribution of the protein.

Purification of α-Gal A from the Conditioned Medium of Stably Transfected Cells

α-Gal A may be purified to near-homogeneity from the cultured cell strains and/or conditioned medium of the cultured cell strains that have been stably transfected to produce the enzyme. α-Gal A can be isolated from α-Gal A containing media using chromatographic steps. For example, 1 or more, e.g., 2, 3, 4, 5 or more chromatographic steps can be used. The different steps of chromatography utilize various separation principles which take advantage of different physical properties of the enzyme to separate α-Gal A from contaminating material. For example, the steps can include: hydrophobic interaction chromatography on butyl Sepharose, ionic interaction on hydroxyapatite, anion exchange chromatography on Q Sepharose and size exclusion chromatography on Superdex 200. Size exclusion chromatography can serve as an effective means to exchange the purified protein into a formulation-compatible buffer.

One purification process includes the use of butyl Sepharose® chromatography as a first step in purification. Other hydrophobic interaction resins, such as Source Iso (Pharmacia), Macro-Prep® Methyl Support (Bio-Rad), TSK Butyl (Tosohaas) or Phenyl Sepharose (Pharmacia) can also be used. The column can be equilibrated in a relatively high concentration of a salt, e.g., 1 M ammonium sulfate or 2 M sodium chloride, e.g., in a buffer of pH 5.6. The sample to be purified can be prepared by adjusting the pit and salt concentration to those of the equilibration buffer. The sample is applied to the column and the column is washed with equilibration buffer to remove unbound material. The α-Gal A is eluted from the column with a lower ionic strength buffer, water, or organic solvent in water, e.g., 20% ethanol or 50% propylene glycol. Alternatively, the α-Gal A can be made to flow through the column by using a lower concentration of salt in the equilibration buffer and in the sample or by using a different pH. Other proteins may bind to the column, resulting in purification of the α-Gal A-containing sample which did not bind the column.

An alternative step of purification can use a cation exchange resin, e.g., SP Sepharose® 6 Fast Flow (Pharmacia), Source 30S (Pharmacia), CM Sepharose® Fast Flow (Pharmacia), Macro-Prep® CM Support (Bio-Rad) or Macro-Prep® High S Support (Bio-Rad), to purify α-Gal A. The "first chromatography step" is the first application of a sample to a chromatography column (all steps associated with the preparation of the sample are excluded). The α-Gal A can hind to the column at pH 4.4. A buffer, such as 10 mM sodium acetate, pH 4.4, 10 mM sodium citrate, pH 4.4, or other buffer with adequate buffering capacity at approximately pH 4.4, can be used to equilibrate the column. The sample to be purified is adjusted to the pH and ionic strength of the equilibration buffer. The sample is applied to the column and the column is washed alter the load to remove unbound material. A salt, such as sodium chloride or potassium chloride, can be used to elute the α-Gal A from the column. Alternatively, the α-Gal A can be eluted from the column with a buffer of higher pH or a combination of higher salt concentration and higher pH. The α-Gal A can also be made to flow through the column during loading by increasing the salt concentration in the equilibration buffer and in the sample load, by running the column at a higher pH, or by a combination of both increased salt and higher pH.

Another step of purification can use a Q Sepharose® 6 Fast Flow for the purification of α-Gal A. Q Sepharose® 6 Fast Flow is a relatively strong anion exchange resin. A weaker anion exchange resin such as DEAE Sepharose® Fast Flow (Pharmacia) or Macro-Prep® DEAB (Bio-Rad) can also be used to purify α-Gal A. The column is equilibrated in a buffer, e.g., 10 mM sodium phosphate, pH 6. The pH of the sample is adjusted to pH 6, and low ionic strength is obtained by dilution or diafiltration of the sample. The sample is applied to the column under conditions that bind α-Gal A. The column is washed with equilibration buffer to remove unbound material. The α-Gal A is eluted with application of salt, e.g., sodium chloride or potassium chloride, or application of a lower pH buffer, or a combination of increased salt and lower pH. The α-Gal A can also be made to flow through the column during loading by increasing the salt concentration in the load or by running the column at a lower pH, or by a combination of both increased salt and lower pH.

Another step of purification can use a Superdex® 200 (Pharmacia) size exclusion chromatography for purification of α-Gal A. Other size exclusion chromatography resins such as Sephacryl® S-200 HR or Bio-Gel® A-1.5 m can also be used to purify α-Gal A. The preferred buffer for size exclusion chromatography is 25 mm sodium phosphate, pH 6.0, containing 0.15 M sodium chloride. Other formulation-compatible buffers can also be used, e.g., 10 mM sodium or potassium citrate. The pH of the buffer can be between pH 5 and pH 7 and should at contain a salt, e.g., sodium chloride or a mixture of sodium chloride and potassium chloride.

Another step of purification can use a chromatofocusing resin such as Polybuffer Exchanger PBE 94 (Pharmacia) to purify α-Gal A. The column is equilibrated at relatively high pH (e.g., pH 7 or above), the pH of the sample to be purified is adjusted to the same pH, and the sample is applied to the column. Proteins are eluted with a decreasing pH gradient to a pH such as pH 4, using a buffer system, e.g., Polybuffer 74 (Pharmacia), which had been adjusted to pH 4.

Alternatively, immunoaffinity chromatography can be used to purify α-Gal A. An appropriate polyclonal or monoclonal antibody to α-Gal A (generated by immunization with α-Gal A or with a peptide derived from the α-Gal A sequence using standard techniques) can be immobilized on an activated coupling resin, e.g., NHS-activated Sepharose® 4 Fast Flow (Pharmacia) or CNBr-activated Sepharose® 4 Fast Flow (Pharmacia). The sample to be purified can be applied to the immobilized antibody column at about pH 6 or pH 7. The column is washed to remove unbound material. α-Gal A is elated from the column with typical reagents utilized for affinity column elution such as low pH, e. g., pH 3, denaturant, e.g., guanidine HCl or thiocyanate, or organic solvent, e.g., 50% propylene glycol in a pH 6 buffer. The purification procedure can also use a metal chelate affinity resin, e.g., Chelating Sepharose® Fast Flow (Pharmacia), to purify α-Gal A. The column is pre-charged with metal ions, e.g., $Cu^{+2}$, $Zn^{+2}$, $Ca^{+2}$, $Mg^{+2}$ or $Cd^{+2}$. The sample to be purified is applied to the column at an appropriate pH, e.g., pH 6 to 7.5, and the column is washed to remove unbound proteins. The bound proteins are eluted by competitive elution with imidazole or histidine or by lowering the pH using sodium citrate or sodium acetate to a pH less than 6, or by introducing chelating agents, such as EDTA or EGTA.

Dosages for Administration of α-Gal A Preparation

The α-Gal A preparations described herein exhibit a desirable circulatory half-life and tissue distribution, e.g., to capillary endothelial cells, renal glomerular epithelial cells (podocytes) and glomerular mesangial cells, and/or cardiac myocytes. Such preparations can be administered in relatively low dosages. For example, the unit dose of administration can be between 0.05-2.0 mg per kilogram body weight (mg/kg). For example, the unit dose can be between 0.05 and 1.0 mg, between 0.5 and 0.5 mg/kg, or between 0.5 and 0.3 mg/kg. Unit doses between 0.05 and 0.29 mg/kg are preferred, e.g., a unit dose of about 0.05, 0.1, 0.15, 0.2, 0.25, mg/kg. Assuming a specific activity of the α-Gal A preparation of between 2 and $4.5 \times 10^6$ U/mg, these values correspond to about $0.1 \times 10^6$ to $1.3 \times 10^6$ U/kg. A preferred unit dose saturates liver uptake of the α-Gal A.

Regularly repeated doses of the protein are necessary over a period of time, e.g., for a period of several months or 1, 2, 3 years or longer, even for the life of the patient. However, the desirable circulatory half-life and tissue distribution of the α-Gal A preparations described herein allow for the administration of the unit dose to a patient at relatively long intervals. For example, a unit dose can be administered no more than once every 7 days, 10 days, 14 days, 21 days, 4 weeks, 6 weeks, 8 weeks, 10 weeks or 12 weeks. A preferred frequency of dosing is biweekly, monthly or bimonthly.

During the time of therapy, a patient can be monitored clinically to evaluate the status of his or her disease. Clinical improvement measured by, for example, improvement in renal or cardiac function or patient's overall well-being (e.g., pain), and laboratory improvement measured by, for example, reductions in urine, plasma, or tissue $Gb_3$ levels, may be used to assess the patient's health status. In the event that clinical improvement is observed after a treatment and monitoring period, the frequency of α-Gal A administration may be reduced. For example, a patient receiving weekly injections of α-Gal A preparation may change to biweekly administration; a patient receiving biweekly injections of an α-Gal A preparation may switch to monthly administration; a patient receiving monthly injections of an α-Gal A preparation may switch to bi-monthly injections. Following such a change in dosing frequency, the patient should be monitored for another period of time, e.g., several years, e.g., a three year period, in order to assess Fabry disease-related clinical and laboratory measures. In a preferred embodiment, the administered dose does not change if a change in dosing frequency is made. This ensures that certain pharmacokinetic parameters (e.g. maximal plasma concentration [$C_{max}$], time to maximal plasma concentration [$t_{max}$], plasma, half-life [$t_{1/2}$], and exposure as measured by area under the curve [AUC]) remain relatively constant following each administered dose. Maintenance of these pharmacokinetic parameters will result in relatively constant levels of receptor-mediated uptake of α-Gal A into tissues as dose frequencies change.

In some embodiments, a patient is clinically evaluated between doses and a determination can be made upon evaluation as to the timing of the next dose.

Subcutaneous injections can be used to maintain longer term exposure to the drug. Dosages of the α-Gal A preparations that are administered by intramuscular injections may be the same or different than those injected subcutaneously. In a preferred embodiment, intramuscular dosages are smaller and administered less frequently. The α-Gal A preparation is preferably administered intravenously, e.g., in a intravenous bolus injection, in a slow push intravenous injection, or by continuous intravenous injection. Continuous IV infusion (e.g., over 2-6 hours) allows the maintenance of specific levels in the blood.

A patient with atypical variant of Fabry disease, e.g., exhibiting predominantly cardiovascular abnormalities or renal involvement, can be treated with these same dosage regiments as described herein. The dose is adjusted as needed. For example, a patient with the cardiac variant phenotype who is treated with α-Gal A enzyme replacement therapy will have a change in the composition of their heart and improved cardiac function following therapy. This change can be measured with standard echocardiography which is able to detect increased left ventricular wall thickness in patients with Fabry disease (Goldman et al., J Am Coll Cardiol 7: 1157-1161 (1986)). Serial echocardiographic measurements of left ventricular wall thickness can be conducted during therapy, and a decrease in ventricular wall size is indicative of a therapeutic response. Patients undergoing α-Gal A enzyme replacement therapy can also be followed with cardiac magnetic resonance imaging (MRI). MRI has the capability to assess the relative composition of a given tissue. For example, cardiac MRI in patients with Fabry disease reveals deposited lipid within the myocardium compared with control patients (Matsui et al., Ani Heart J 117; 472-474. (1989)). Serial cardiac MRI evaluations in a patient undergoing enzyme replacement therapy can reveal a change in the lipid deposition within a patient's heart. Patients with the renal variant phenotype can also benefit from α-Gal A enzyme replacement therapy.

The effect of therapy can be measured by standard tests of renal function, such as 24-hour urine protein level, creatinine clearance, and glomerular filtration rate.

Pharmaceutical Compositions

The α-Gal A preparations described herein are substantially free of non-α-Gal A proteins, such as albumin, non-α-Gal A proteins produced by the host cell, or proteins isolated from animal tissue or fluid. The preparation preferably comprises part of an aqueous or physiologically compatible fluid suspension or solution. The carrier or vehicle is physiologically compatible so that, in addition to delivery of the desired preparation to the patient, it does not otherwise adversely affect the patient's electrolyte and/or volume balance. Useful solutions for parenteral administration may be prepared by any of the methods well known in the pharmaceutical art (See, e.g., REMINGTON'S PHARMACEUTICAL SCIENCES Gennaro, A., ed., Mack Pub., 1990).

Non-parenteral formulations, such as suppositories and oral formulations, can also be used. Preferably the formulation contains an excipient. Pharmaceutically acceptable excipients for α-Gal A which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (PEG); glycerol; glycine or other amino acids; and lipids. Preferred excipients include mannitol, sorbitol, glycerol, amino acids, lipids, EDTA, EGTA, sodium chloride, polyethylene glycol, polyvinylpyrrollidone, dextran, or combinations of any of these excipients.

In another embodiment, the formulation further comprises a non-ionic detergent. Preferred non-ionic detergents include Polysorbate 20, Polysorbate 80, Triton X-100™, Triton X-114™, Notidet P-40™, Octyl α-glucoside, Octyl β-glucoside, Brij 35, Pluronic™, Poloxamer 188 (a.k.a. Poloxalkol) and Tween 20™. In a preferred embodiment, the non-ionic detergent comprises Polysorbate 20 or Polysorbate 80.

A preferred formulation further comprises phosphate-buffered saline, e.g., at pH 6. Buffer systems for use with α-Gal A preparations include citrate; acetate; bicarbonate; and phosphate buffers (all available from Sigma). Phosphate buffer is a preferred embodiment. A preferred pH range for α-Gal A preparations is pH 4.5-7.4.

For lyophilization of α-Gal A preparations, the protein concentration can be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

Formulations for administration may include glycerol and other compositions of high viscosity to help maintain the agent at the desired locus. Biocompatible polymers, preferably bioresorbable, biocompatible polymers (including, e.g., hyaluronic acid, collagen, polybutyrate, lactide, and glycolide polymers and lactide/glycolide copolymers) may be useful excipients to control the release of the agent in vivo. Formulations for parenteral administration may include glycocholate for buccal administration, methoxysalicylate for rectal administration, or cutnic acid for vaginal administration. Suppositories for rectal administration may be prepared by mixing an α-Gal A preparation of the invention with a non-irritating excipient such as cocoa butter or other compositions that are solid at room temperature and liquid at body temperatures.

Formulations for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 grant per cubic centimeter and mean diameters exceeding 5 μm efficiently deliver inhaled therapeutics into the systemic circulation. Such particles are inspired deep into the lungs and escape the lungs' natural clearance mechanisms until the inhaled particles deliver their therapeutic payload. (Edwards et al., Science 276: 1868-1872 (1997)). α-Gal A preparations of the present invention can be administered in aerosolized form, for example by using methods of preparation and formulations as described in U.S. Pat. Nos. 5,654,007, 5,780,014, and 5,814,607, each incorporated herein by reference.

Formulation for intranasal administration may include oily solutions for administration in the form of nasal drops, or as a gel to be applied intranasally.

Formulations for topical administration to the skin surface may be prepared by dispersing the α-Gal A preparation with a dermatological acceptable carrier such as a lotion, cream, ointment, or soap. Particularly useful are carriers capable of forming a film or layer over the skin to localize application and inhibit removal. For topical administration to internal tissue surfaces, the α-Gal A preparation may be dispersed in a liquid tissue adhesive or other substance known to enhance adsorption to a tissue surface. For example, several mucosal adhesives and buccal tablets have been described for transmucosal drug delivery, such as in U.S. Pat. Nos. 4,740,365, 4,764,378, and 5,780,045, each incorporated herein by reference.

Hydroxypropylcellulose or fibrinogen/thrombin solutions may also be incorporated. Alternatively, tissue-coating solutions, such as pectin-containing formulations may be used. The preparations of the invention may be provided in containers suitable for maintaining sterility, protecting the activity of the active ingredients during proper distribution and storage, and providing convenient and effective accessibility of the preparation for administration to a patient. An injectable formulation of an α-Gal A preparation might be supplied in a stoppered vial suitable for withdrawal of the contents using a needle and syringe. The vial would be intended for either single use or multiple uses. The preparation can also be supplied as a prefilled syringe. In some instances, the contents would be supplied in liquid formulation, while in others they would be supplied in a dry or lyophilized state, which in some instances would require reconstitution with a standard or a supplied diluent to a liquid state. Where the preparation is supplied as a liquid for intravenous administration, it might be provided in a sterile bag or container suitable for connection to an intravenous administration line or catheter. In preferred embodiments, the preparations of the invention are supplied in either liquid or powdered formulations in devices which conveniently administer a predetermined dose of the preparation; examples of such devices include a needle-less injector for either subcutaneous or intramuscular injection, and a metered aerosol delivery device. In other instances, the preparation may be supplied in a form suitable for sustained release, such as in a patch or dressing to be applied to the skin for transdermal administration, or via erodible devices for transmucosal administration. In instances where the preparation is orally administered in tablet or pill form, the preparation might be supplied in a bottle with a removable cover. The containers may be labeled with information such as the type of preparation, the name of the manufacturer or distributor, the indication, the suggested dosage, instructions for proper storage, or instructions for administration.

Methods of Administration of α-Gal A Preparation

The α-Gal A preparations described herein may be administered by any route which is compatible with the α-Gal A preparation. The purified α-Gal A preparation can be administered to individuals who produce insufficient or defective α-Gal A protein or who may benefit from α-Gal A therapy. Therapeutic preparations of the present invention may be provided to an individual by any suitable means, directly (e.g., locally, as by injection, implantation or topical administration to a tissue locus) or systemically (e.g., orally or parenterally).

The preferred route of administration is intravenous. Other routes of administration may be oral or parenteral, including subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation. Intrapulmonary delivery methods, apparatus and drug preparation are described, for example, in U.S. Pat. Nos. 5,785,049, 5,780,019, and 5,775,320, each incorporated herein by reference. A preferred method of intradermal delivery is by iontophoretic delivery via patches; one example of such delivery is taught in U.S. Pat. No. 5,843,015, which is incorporated herein by reference.

A particularly useful route of administration is by subcutaneous injection. An α-Gal A preparation of the present invention is formulated such that the total required dose may be administered in a single injection of one or two milliliters. In order to allow an injection volume of one or two milliliters, an α-Gal A preparation of the present invention may be formulated at a concentration in which the preferred dose is delivered in a volume of one to two milliliters, or the α-Gal A preparation may be formulated in a lyophilized form, which is reconstituted in water or an appropriate physiologically compatible buffer prior to administration. Subcutaneous injections of α-Gal A preparations have the advantages of being convenient for the patient, in particular by allowing self-administration, while also resulting in a prolonged plasma half-life as compared to, for example, intravenous administration. A prolongation in plasma half-life results in maintenance of effective plasma α-Gal A levels over longer time periods, the benefit of which is to increase the exposure of clinically affected tissues to the injected α-Gal A and, as a result, may increase the uptake of α-Gal A into such tissues. This allows a more beneficial effect to the patient and/or a reduction in the frequency of administration. Furthermore, a variety of devices designed for patient convenience, such as refillable injection pens and needle-less injection devices, may be used with the α-Gal A preparations of the present invention as discussed herein.

Administration may be by periodic injections of a bolus of the preparation, or may be administered by intravenous or intraperitoneal administration from a reservoir which is external (e.g., an IV bag) or internal (e.g., a bioerodable implant, a bioartificial organ, or a population of implanted α-Gal A production cells). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the α-Gal A preparation described above can administered in these methods.

The route of administration and the amount of protein delivered can be determined by factors that are well within the ability of skilled artisans to assess. Furthermore, skilled artisans are aware that the route of administration and dosage of a therapeutic protein may be varied for a given patient until a therapeutic dosage level is obtained.

All patents and publications cited in this specification are incorporated by reference.

EXAMPLES

Example 1: Preparation and Use of Constructs Designed to Deliver and Express α-Gal A 1.1: Preparation of Gene-Activated α-Gal A (GA-GAL)
Production of gene-activated α-Gal A (GA-GAL) occurred by insertion of regulatory and structural DNA sequences upstream of the human α-Gal A coding sequence, using the GA technology substantially as described in U.S. Pat. No. 5,733,761, herein incorporated by reference. The precise insertion of the gene-activating sequence occurs as a result of homologous recombination between DNA present on a transfected DNA fragment and genomic DNA sequences upstream of the α-Gal A locus in a human cell. The gene-activating sequence itself contains α-Gal A coding sequence up to, but not including, the signal peptide cleavage site. Cells containing an activated α-Gal A locus were isolated and subjected to drug selection to isolate cells with increased GA-GAL production.

A targeting DNA fragment containing an appropriate gene-activating sequence was introduced into host human cell lines by electroporation. One such cell line is HT-1080, a certified cell line available from ATCC (Manassas, Va.). The gene activation plasmid (targeting construct) pGA213C containing such a DNA fragment is shown in FIG. 3A. This plasmid contains sequences designed to activate a portion of the endogenous α-Gal A locus in the host cell line, and contains sequences encoding the signal peptide, but not human α-Gal A. The targeting construct also contains expression cassettes for the bacterial neo and mouse dhfr genes. These allow for the selection of stably integrated targeting fragments (via the neo gene) and for subsequent selection of the dhfr gene using step-wise methotrexate (MTX) selection.

Figure 3B:
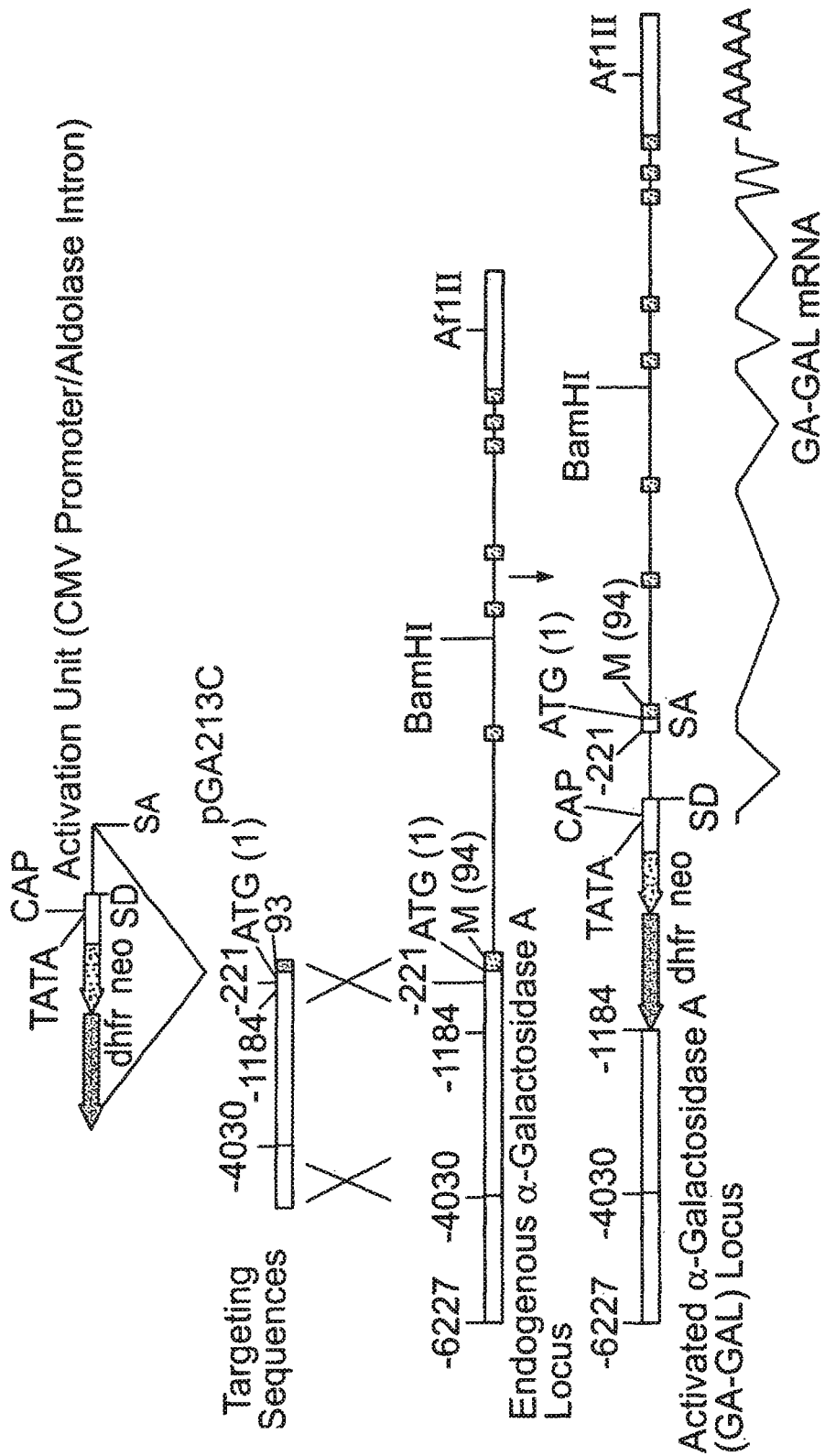
FIG. 3B is a diagrammatic representation of the targeting construct, pGA213C, and homologous recombination with the endogenous α-Gal A locus, pGA213C is depicted as targeting sequences aligned above corresponding sequences on the X-chromosomal α-Gal A locus. Positions relative to the methionine initiation codon, ATG, are indicated by the numbers above the linear maps. The activation unit containing murine dhfr, bacterial neo, and CMV promoter/aldolase intron sequences is shown above the position (−221) into which they were inserted by DNA cloning. α-Gal A coding sequences are indicated by the darkened boxes. α-Gal A non-coding genomic sequences are indicated by the lightly filled boxes. Large arrowheads indicate the direction of transcription for dhfr and neo expression.

In addition, pGA213C contains sequences designed to target chromosomal sequences upstream of the endogenous α-Gal A locus by homologous recombination. Homologous recombination between the endogenous α-Gal A locus and the 9.6 kb DNA fragment of pGA213 C is shown in FIG. 3B.

pGA213C was constructed to delete 962 bp of genomic sequences extending from positions −1183 to −222 relative to the methionine initiation codon of α-Gal A, upon homologous recombination of the pGA213C fragment with the X-chromosomal α-Gal A locus. Transcriptional activation of the α-Gal A locus occurs through precise targeting of the exogenous regulatory sequences upstream of the α-Gal A coding region. The resulting GA-GAL locus cause transcription to initiate from the CMV promoter and to proceed through CMV exon 1, the aldolase intron and the seven exons and six introns of the α-Gal A coding sequence. Splicing of the large precursor mRNA joins the exogenous CMV exon (inserted by targeting) with the entire endogenous first exon of α-Gal A transcript. Translation of the GA-GAL mRNA results in pre GA-GAL with a thirty one amino acid signal peptide. Upon secretion from the host cell, the signal peptide is removed. Correctly targeted cell lines are first identified by polymerase chain reaction screening for the presence of the GA-GAL mRNA. Clones producing the GA-GAL mRNA are also found to secrete enzymatically active α-Gal A into the culture media. Subsequent confirmation of targeting events is accomplished by restriction enzyme digestion and Southern blot hybridization analysis of genomic DNA.

Cells were exposed to stepwise methotrexate ("MTX") selection. Following selection in 0.05 μM MTX, a clone of cells was isolated and subjected to 0.1 μM MTX selection. From this process a pool of cells resistant to 0.1 μM MTX was isolated (cell line RAG001) and expanded in culture.

1.2: Preparation of Other Constructs to Express α-Gal A

Two other expression plasmids, pXAG-16 and pXAG-28, were constructed. These plasmids contain human α-Gal A cDNA encoding the 398 amino acids of the α-Gal A enzyme (without the α-Gal A signal peptide); the human growth hon-none (hGH) signal peptide genomic DNA sequence, which is interrupted by the first intron of the hGH gene; and the untranslated sequence (UTS) of the hGH gene, which contains a signal for polyadenylation. Plasmid pXAG-16 has the human cytomegalovirus immediate-early (CMV IE) promoter and first intron (flanked by non-coding exon sequences), while pXAG-28 is driven by the collagen 1α2 promoter and exon 1, and also contains the β-actin gene's 5'UTS, which contains the first intron of the β-actin gene.

In order to express α-Gal A in fibroblasts, secondary fibroblasts were cultured and transfected according to published procedures (Selden et al., WO 93/09222). The plasmids pXAG-13, pXAG-16 and pXAG-28 were transfected by electroporation into human foreskin fibroblasts to generate stably transfected clonal cell strains, and the resulting α-Gal A expression levels were monitored. Secretion of α-Gal A by normal foreskin fibroblasts is in the range of 2-10 units/$10^6$ cells/24 hours. In contrast, the transfected fibroblasts displayed mean expression levels as shown in the table below.

| Mean α-Gal A expression levels (±standard deviation) | |
|---|---|
| pXAG-13: | 420 ± 344 U/$10^6$ cells/day |
| | N = 26 clonal strains |
| | (range 3-1133 U/$10^6$ cells/day) |
| pXAG-16: | 2,051 ± 1253 U/$10^6$ cells/day |
| | N = 24 clonal strains |
| | (range 422-5200 U/$10^6$ cells/day) |
| pXAG-28: | 141 ± 131 U/$10^6$ cells/day |
| | N = 38 clonal strains |
| | (range 20-616 U/$10^6$ cells/day) |

These data show that all three expression constructs are capable of increasing α-Gal A expression many times that of nontransfected fibroblasts. Expression by fibroblasts stably transfected with pXAG-13, which encodes α-Gal A linked to the α-Gal A signal peptide, was substantially lower than expression by fibroblasts transfected with pXAG-16, which differs only in that the signal peptide is the hGH signal peptide, the coding sequence of which is interrupted by the first intron of the hGH gene.

Cell strains desirable for gene therapy or for use in generation of material for purification of α-Gal A should display stable growth and expression over several passages. Data from the cell strains which were stably transfected with the α-Gal A expression construct showed that α-Gal A expression is stably maintained during serial passage.

Example 2: Structural Comparison of α-Gal A Produced in Human Cells Vs. CHO Cells This example compares the structure of Replagal™, an α-Gal A preparation produced in human cells vs. Fabrazyme™, an α-Gal A preparation produced in CHO cells. The preparations were compared with respect to isoelectric point, molecular weight, and carbohydrate, phosphorylation and sialylation profile.

Isoelectric Point

Replagal™ and Fabrazyme™ were analyzed by denaturing isoelectric focusing (5% gels, pH range 3 to 7, 6 M urea) followed by Western blotting. The preparations were also analyzed by native isoelectric focusing (Novex 5% gels, pH range 3 to 7) following by Coomassie Blue staining. The overall pI range of the 2 preparations were similar, although the relative intensities of the banding patterns were different.

This indicates that the glycoforms present in each preparation differ in charge distribution, with Fabrazyme™ containing a greater proportion of lower pI (more negatively charged) glycoforms than Replagal™.

Molecular Weight

Replagal™ and Fabrazyme™ were analyzed by SDS-PAGE (8-16% polyacrylamide gel, reduced samples) followed by Coomassie Blue staining. The molecular weights of the preparations were similar. However, the lower (approximately 45 kD) glycoform band of Fabrazyme™ is more distinct compared to that of Replagal™, while Replagal™ exhibits a broader size distribution.

Figure 6:
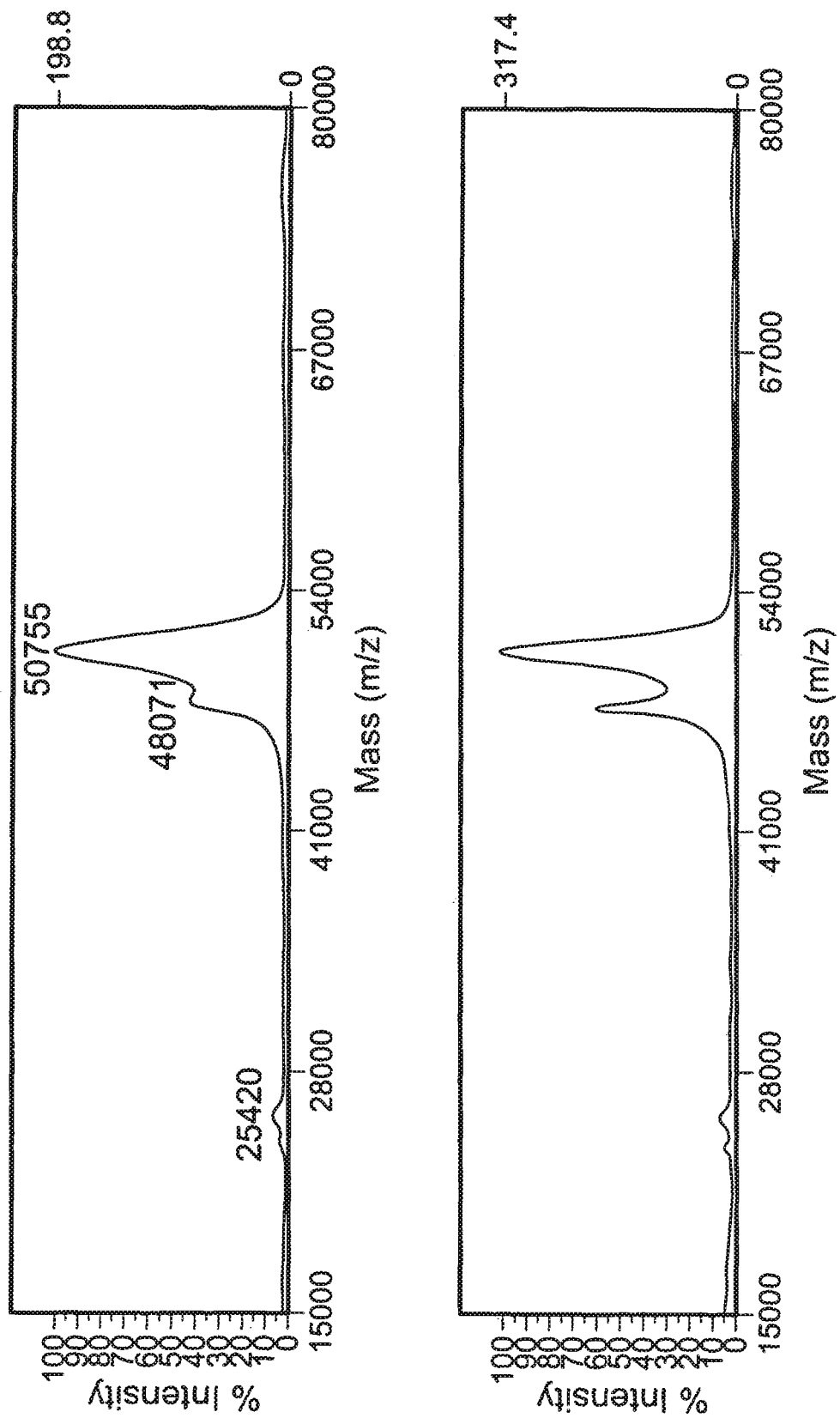
FIG. 6 shows the molecular masses of α-Gal A made in human cells (Replagal™) (top) and α-Gal A made in CHO cells (Fabrazyme™) (bottom) as determined by MALDI-TOF mass spectroscopy. The maximum of the major broad peak is at 50,755 and 50,705 Da, respectively, consistent with the expected molecular weight of the glycosylated monomer. A leading shoulder at approximately 48,071 Da and 47,667 Da is present, representing the lower molecular weight glycoforms for Replagal™ and Fabrazyme™, respectively. The leading shoulder, corresponding to the lower molecular weight glycoforms, is much more distinct in the spectrum of Fabrazyme™.

In FIG. 6, The molecular masses of Replagal™ (top) and Fabrazyme™ (bottom) were determined by MALDI-TOF mass spectroscopy. The maximum of the major broad peak is at 50,755 and 50,705 Da, respectively, consistent with the expected molecular weight of the glycosylated monomer. A leading shoulder at approximately 48,071 Da and 47,667 Da is present, representing the lower molecular weight glycoforms for Replagal™ and Fabrazyme™, respectively. The leading shoulder, corresponding to the lower molecular weight glycoforms, is much more distinct in the spectrum of Fabrazyme™.

Figure 8:
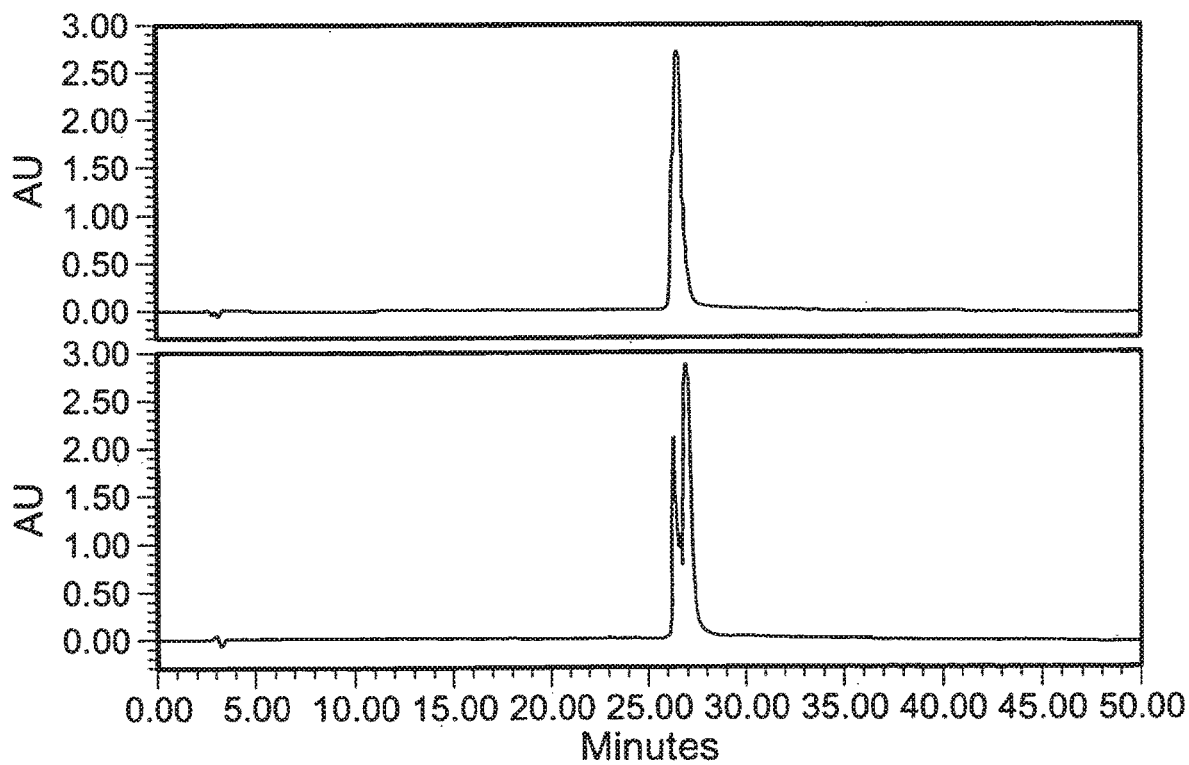
FIG. 8 is a chromatogram of Fabrazyme™ (top) and Replagal™ (bottom) as analyzed by reversed phase HPLC using a C4 reversed phase column (Vydac). Chromatograms obtained at 214 nm are shown. The leading shoulder, corresponding to the lower molecular weight glycoforms, is much more pronounced in Fabrazyme™.

FIG. 8 shows Fabrazyme™ (top) and Replagal™ (bottom) as analyzed by reversed phase HPLC using a C4 reversed phase column (Vydac). Chromatograms obtained at 214 nm are shown. The leading shoulder, corresponding to the lower molecular weight glycoforms, is much more pronounced in Fabrazyme™.

Cellular Internalization

Figure 5:
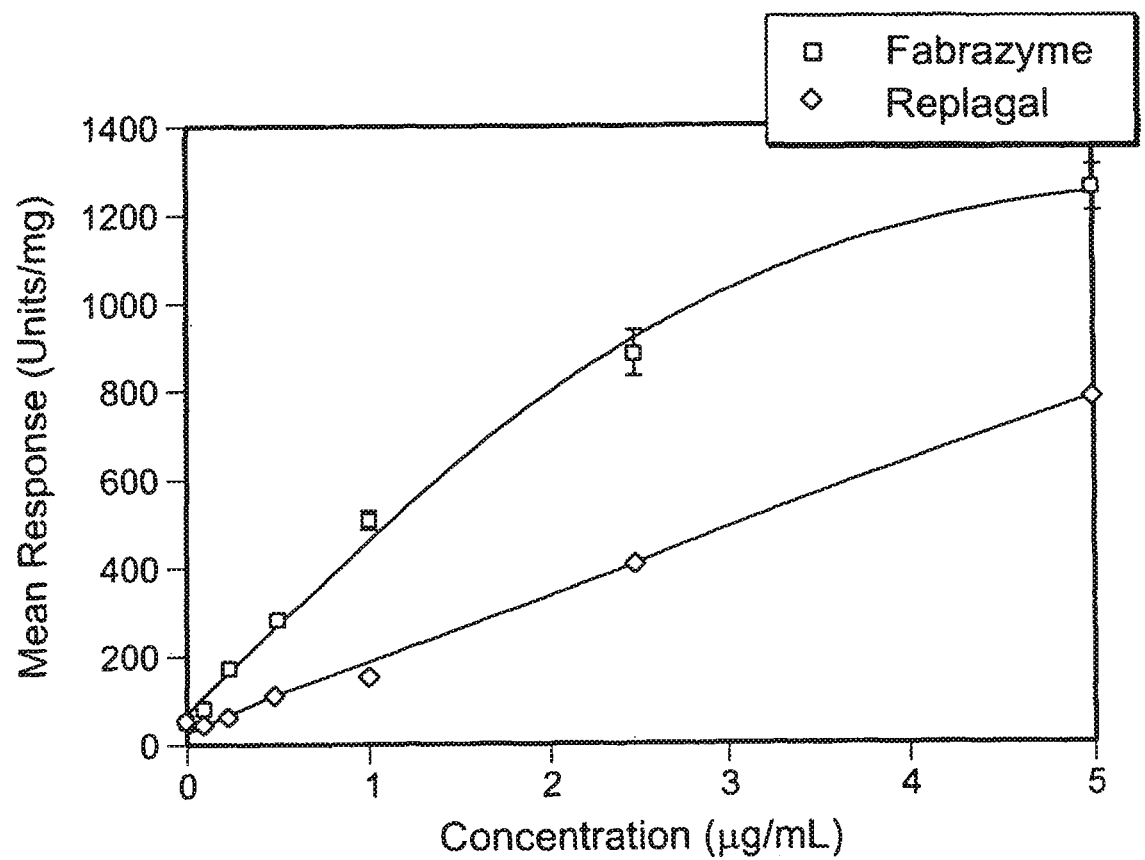
FIG. 5. is a graph showing internalization of α-Gal A made in human cells (Replagal™) and α-Gal A made in CHO cells (Fabrazyme™) into cells. Normal human fibroblasts were incubated in multi-well culture plates for 6 hours in the absence (control, not shown) or presence of Replagal™ or Fabrazyme™. This internalization is mannose-6-phosphate inhibitable, indicating that internalization is predominantly via mannose-6-phosphate receptors. The results indicate that Replagal™ and Fabrazyme™ are not internalized comparably by the fibroblasts. Fabrazyme™ is cleared more rapidly than Replagal™ by mannose-6-phosphate receptor-mediated internalization.

Normal human fibroblasts were incubated in multi-well culture plates for 6 hours in the absence (control, not shown) or presence of Replagal™ or Fabrazyme™. This internalization is mannose-6-phosphate inhibitable, indicating that internalization is predominantly via mannose-6-phosphate receptors. The results indicate that Replagal™ and Fabrazyme™ are not internalized comparably by the fibroblasts. Fabrazyme™ is internalized more rapidly than Replagal™ by mannose-6-phosphate receptor-mediated internalization (see FIG. 5).

Glycan Composition and Characterization

Figure 7:
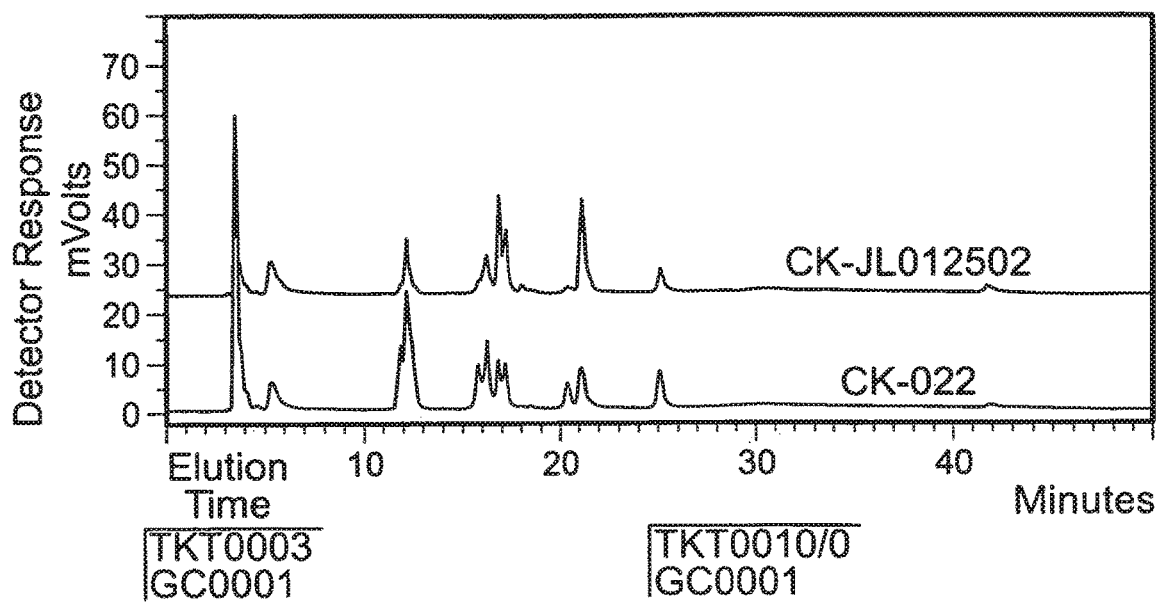
FIG. 7 is a charge profile of the glycans released from α-Gal A made in human cells (Replagal™) (bottom) and α-Gal A made in CHO cells (Fabrazyme™) (top). Glycans were derivatized with a fluorescent probe and compared by ion exchange chromatography on a GlycoSep™ C column. The results show that Replagal™ has a higher proportion of neutral and mono-charged glycans, and Fabrazyme™ has a higher proportion of tri-charged glycans.

FIG. 7 shows charge profiles of the glycans released from Replagal™ (bottom) and Fabrazyme™ (top). Glycans were derivatized with a fluorescent probe and compared by ion exchange chromatography on a GlycoSep™ C column. The results show that Replagal™ has a higher proportion of neutral and mono-charged glycans, and Fabrazyme™ has a higher proportion of tri-charged glycans.

Figure 4:
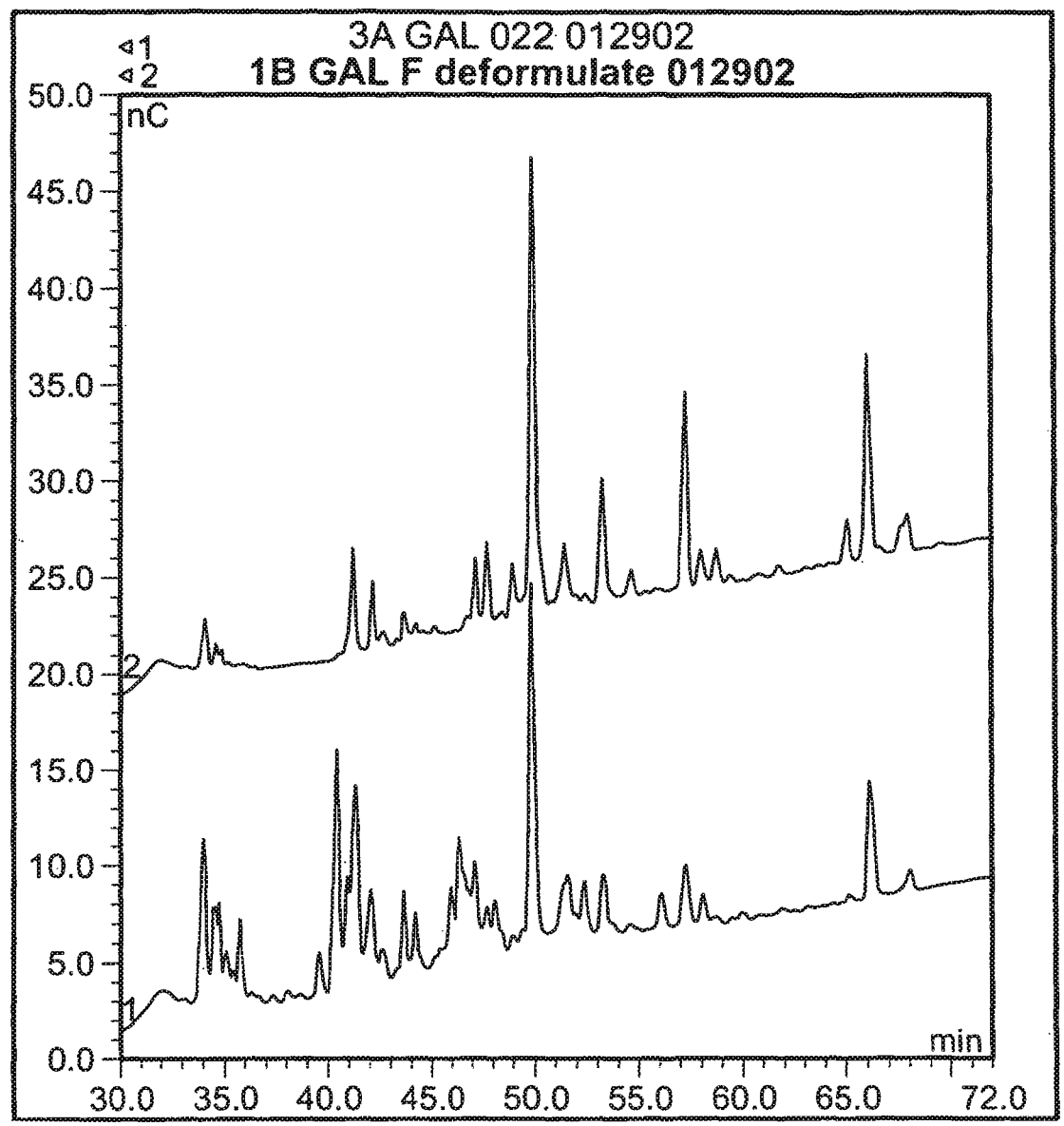
FIG. 4. is a chromatograph showing glycans released from α-Gal A made in human cells (Replagal™) vs α-Gal A made in CHO cells (Fabrazyme™). Both preparations were analyzed using HPAE-PAD on a Dionex BioLC Carbohydrate System. The glycan profiles indicate that there are significant differences in the glycan chains of Replagal™ (top) and Fabrazyme™ (bottom). Fabrazyme™ is enriched in phosphorylated structures (peaks eluting at 65-69 minutes) and more highly sialylated structures (tetra-sialylated structures elating at 56-60 minutes and tri-sialylated structures eluting at 51-55 minutes) as compared to Replagal™. Replagal™ is enriched in neutral (peaks at 33-36 minutes), mono-sialylated structures (peaks at 39-44 minutes) and di-sialylated structures (peaks at 45-49 minutes).

Table 1 shows a glycan peak area comparison. Glycans released from Replagal™ and Fabrazyme™ were analyzed using HPAE-PAD as shown in FIG. 4. Integration of peaks was performed to quantify the percentages of the various peak groups. The tabulated data demonstrate a higher proportion of phosphorylated glycans in Fabrazyme™, and a higher proportion of neutral glycans and a higher total proportion of sialylated glycans in Replagal™.

Table 2 shows charge profile results. Charge profiles of glycans released from Replagal™ and Fabrazyme™ were derivatized and separated as described in FIG. 7. CK-022 and CK-006 are 2 different Replagal™ preparations, while CK-JL012502 is a preparation of Fabrazyme™. Glycans from each product were assayed in duplicate. As shown in the table, the Replagal™ preparations have higher proportions of glycans that are neutral or carry 1 charge, while Fabrazyme™ contains a higher proportion glycans with 2 or 3 charges.

Table 3 shows the desialylated profile results. Charge profiles of glycans released from Replagal™ and Fabrazyme™ were desialylated, followed by derivatization and separation as described in FIG. 7. CK-022 and CK-006 are 2 different Replagal™ preparations, while CK-JL012502 is a preparation of Fabrazyme™. Glycans from each product were assayed in duplicate. As shown in the table, the Replagal™ preparations have lower proportions of residual charged glycans after desialylation, indicating that Fabrazyme™ has a higher proportion of phosphorylated (sialidase-resistant) glycans.

Example 3: Interspecies Scaling of Pharmacokinetics of α-Gal A (Replagal™) Made in Human Cells The purpose of this example was to compare pharmacokinetic parameters derived from animal models with human pharmacokinetic results.

Animals (mice, rats, dogs, rabbits and monkeys) received single intravenous bolus injections of Replagal™. Blood samples were collected over a 24 hour period, processed to serum, and analyzed for α-Gal A enzyme activity using an in vitro fluorescence assay. Serum concentration profiles were analyzed using either a 2-compartment model or a non-compartmental model to estimate pharmacokinetic parameters.

Blood samples were collected from male Fabry patients receiving their initial 40 minute infusion of Replagal™. Blood samples were processed to either plasma or serum and analyzed for α-Gal A enzyme activity. Serum concentration profiles were analyzed using a noncompartment model to estimate pharmacokinetic parameters.

Liver biopsies were taken 44 hours after dosing from male Fabry patients in the Phase I trial. Tissue samples were processed and analyzed for concentration of administered α-Gal A as previously described (Schiffman and Brady et al. (2000) Proc. Natl. Acad. Sci. USA 97:365-370). The amount of administered dose recovered in each patient's liver was calculated using the concentration of α-Gal A in each liver biopsy and each patient's estimated liver weight.

Figure 9:
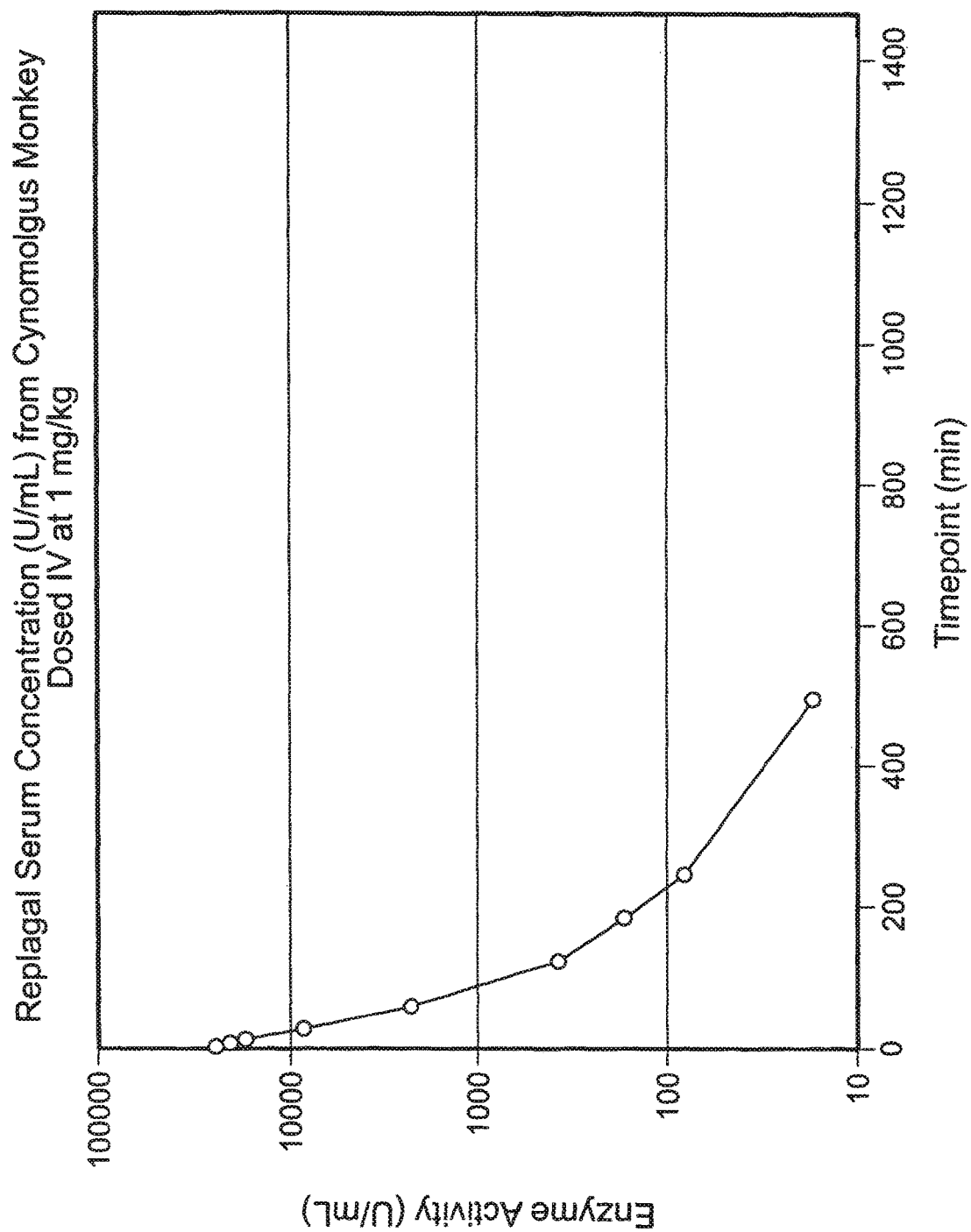
FIG. 9 is a graph showing serum concentration (U/ml) of α-Gal A (Replagal™) made in human cells from Cynomolgus Monkey dosed IV at 1 mg/kg.
Figure 10:
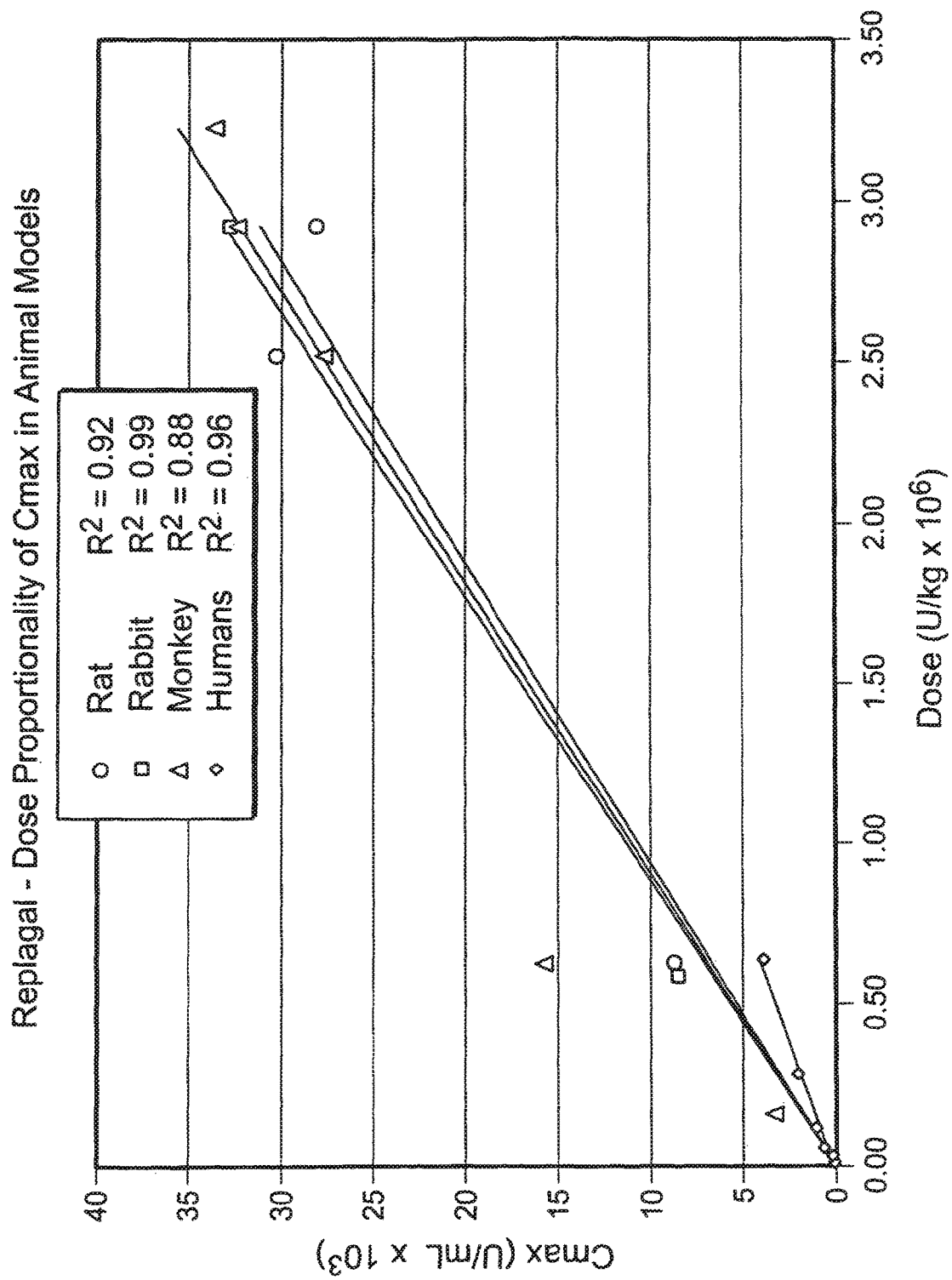
FIG. 10 is a graph showing dose proportionality of $C_{max}$ in animal models of α-Gal A (Replagal™) made in human cells.
Figure 11:
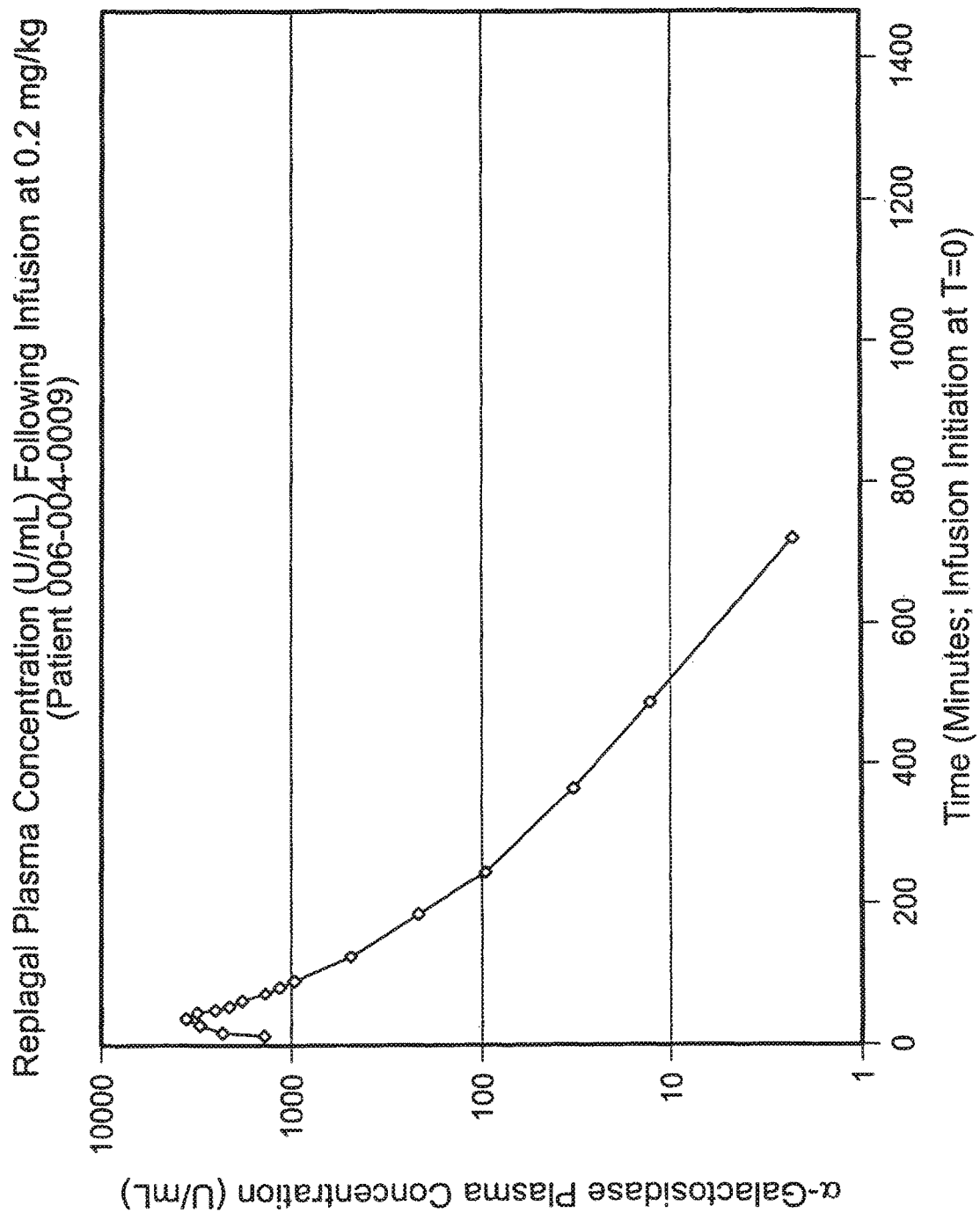
FIG. 11 is a graph showing Replagal™ plasma concentration (U/ml) following infusion at 0.2 mg/kg in a human subject.
Figure 12:
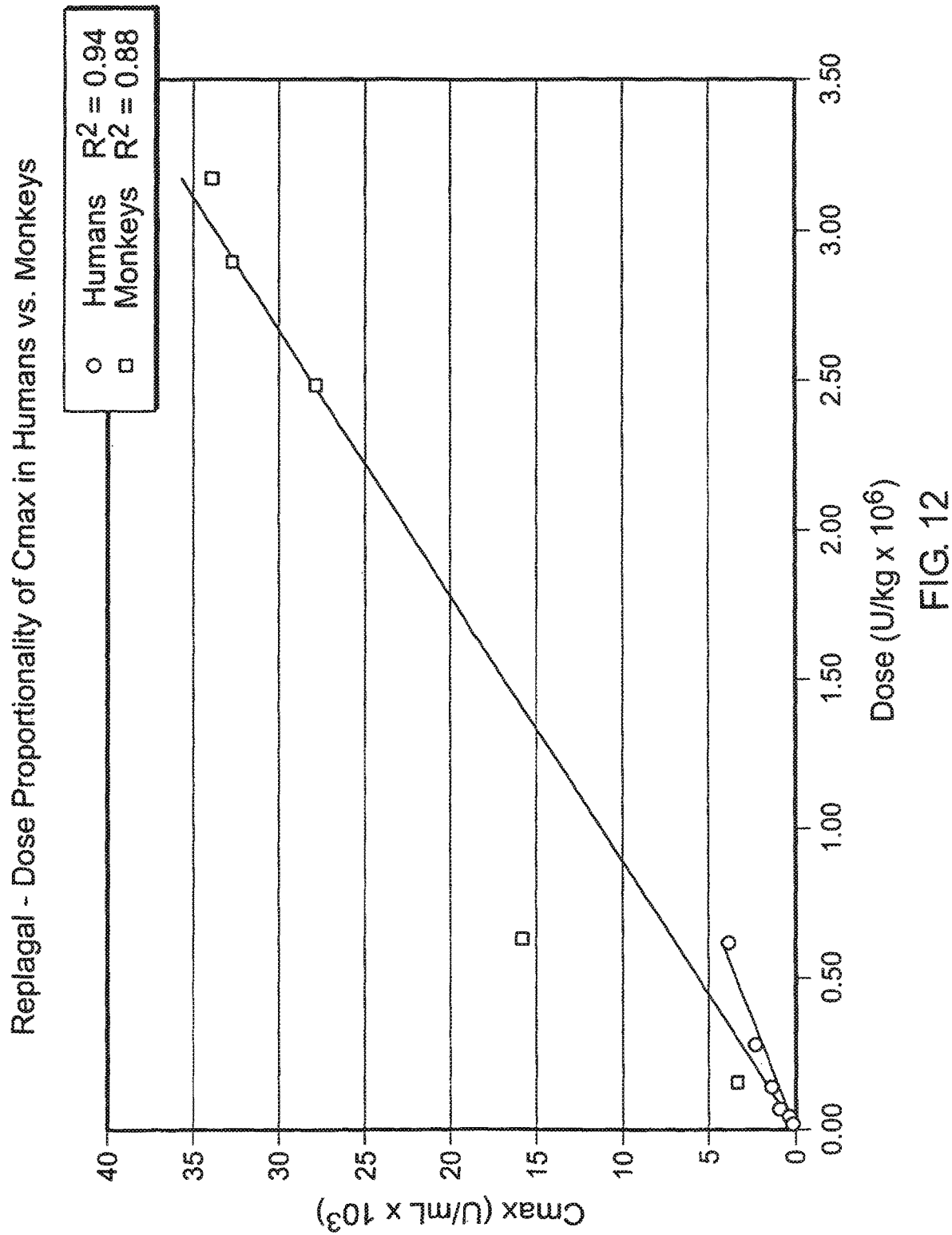
FIG. 12 is a graph showing dose proportionality of $C_{max}$ in humans vs. monkey of α-Gal A (Replagal™) made in human cells.
Figure 13:
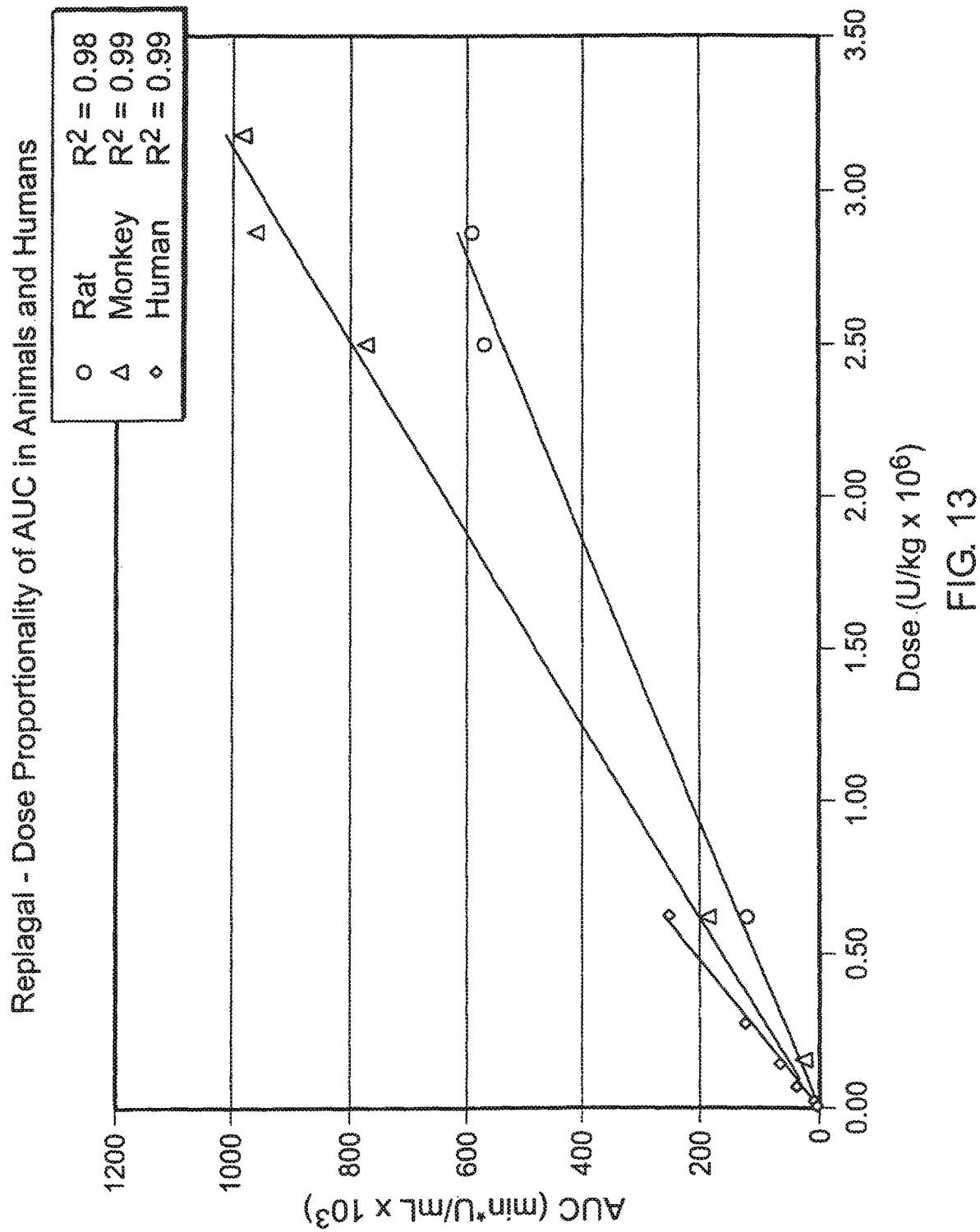
FIG. 13 is a graph showing dose proportionality of area under the curve (AUC) in animal and humans for α-Gal A (Replagal™) made in human cells.

Replagal™ had a biphasic serum elimination profile following a single IV dose in rats, rabbits and monkeys (FIG. 9 illustrates the profile in cynomolgus monkey). $C_{max}$ was proportional to dose for these three animal species (FIG. 10). Replagal™ also had a biphasic serum elimination profile in Fabry patients following a 40 minute infusion (FIG. 11). $C_{max}$ was also dose proportional in humans (FIG. 12). Replagal™ was eliminated by 24 hours after dosing in all species. AUC (area under the curve) increased linearly with dose in animals and humans over a dose range of 0.017 to $3.2 \times 10^6$ U/kg (FIG. 13). The dose range in U/kg corresponds to a range of 0.007 to 0.2 mg/kg in humans and 0.0625 to 1 mg/kg in animals.

Physiological parameters in mammals follow allometric scaling equations based on body weight, $Y=a (BW)^b$ (Table 4). The exponent in the scaling equation can be near 1.0 (e.g., blood volume) but varies between 0.6 and 0.8 for drug or protein clearance.

The allometric scaling equation of Replagal™ (mL/min) was based on pharmacokinetic studies in mice, rats, rabbits, large and small cynomolgus monkeys, and Fabry patients. Serum clearance followed the allometric scaling equation with an exponent of 0.92. (Table 5). The increased exponent for Replagal™ serum clearance in comparison to other drug products or proteins provides support for M6P receptor clearance of Replagal™.

Figure 14:
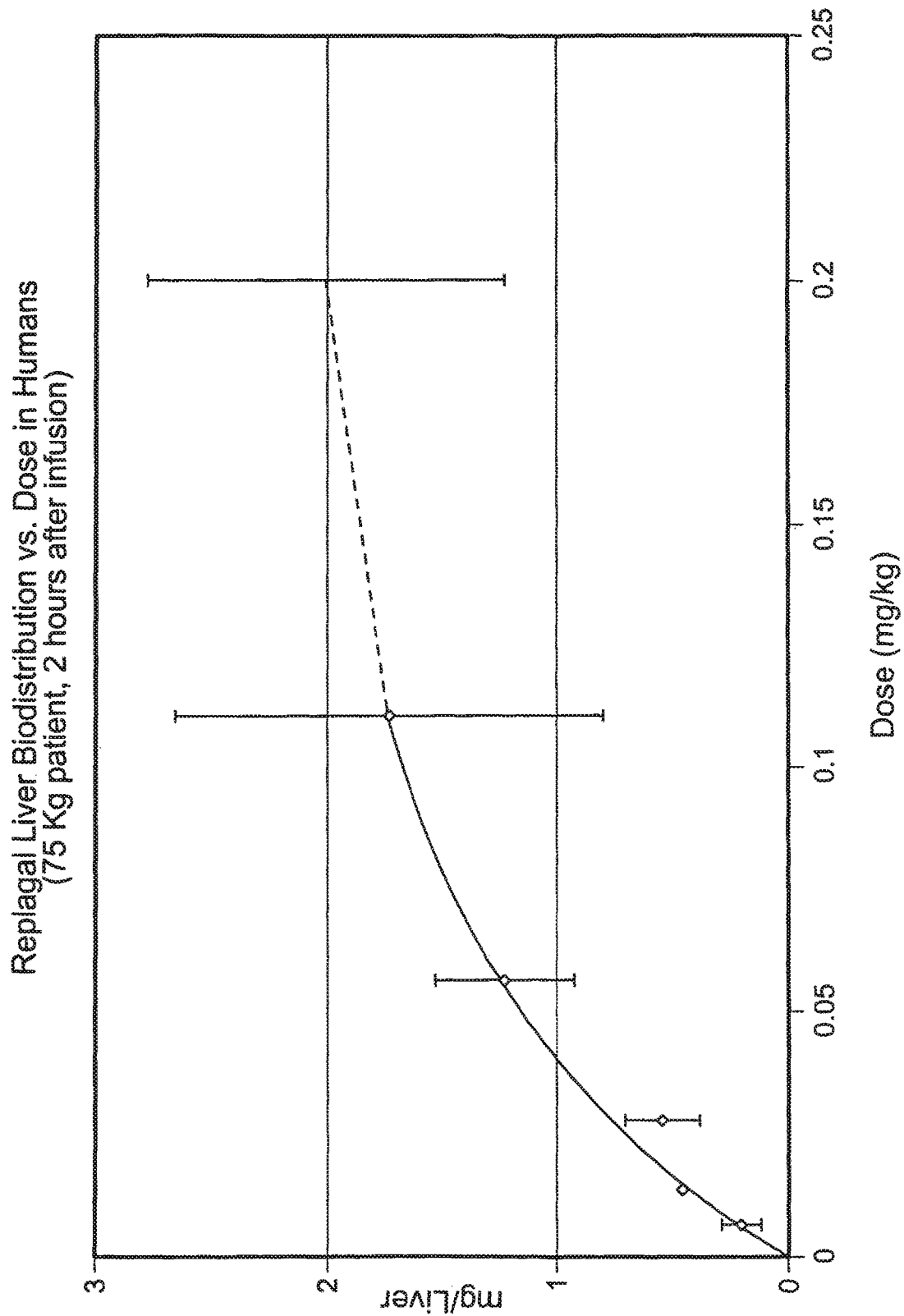
FIG. 14 is a graph showing liver distribution vs. dose in humans of an α-Gal A preparation (Replagal™) made in human cells.

The percent of administered Replagal™ found in a patient's liver decreased as the dose increased on a mg/kg basis (Table 6). At the two lowest doses, 0.007 and 0.014 mg/kg, the percent of Replagal™ recovered in the liver 44 hours after dosing was approximately 25 to 30%. In contrast, at 0.11 mg/kg, only 14% of administered Replagal™ was found in the liver. Saturation of liver uptake of Replagal™ occurred when maximum drug product concentrations ($C_{max}$) exceeded the Kd for the M6P receptor ($2\times10^{-9}$ M). Based on these results, the estimated amount of the commercial dose of Replagal™ (0.2 mg/kg) taken into liver is approximately 2 mg for a 75 mg patient (FIG. 14). the remainder of the dose (13 mg) would then be available for uptake into tissues other than liver.

Thus, single dose pharmacokinetics in animal models provided a good prediction of Replagal™ pharmacokinetics in Fabry patients. The mechanism of clearance of Replagal™ from blood is predominantly through M6P receptors which are found in tissues throughout the body. The exponent for the allometric scaling equation for serum or plasma clearance of Replagal™, 0.92, is greater than that observed for other drug products or proteins. The increased exponent provides support for M6P receptor clearance of Replagal™. Saturation of human liver receptors was observed when $C_{max}$ exceeded the Kd of the M6P receptor (doses of 0.056 mg/kg and higher).

Example 4: Pharmacokinetics of Replagal™ in Male and Female Fabry Patients

The primary purpose of this evaluation was to compare Replagal™ pharmacokinetic properties in male and female Fabry patients. A secondary objective was to compare pharmacokinetic properties between patients treated with Replagal™ and Fabrazyme™.

Blood samples were collected from male and female Fabry patients receiving their initial 40 minute infusion of Replagal from TKT006 (NIH), TKT007 (UK) and TKT014 (GERMANY). Blood samples were processed to serum (TKT007 and TKT014 samples) or plasma (TKT006 samples) and analyzed for α-galactosidase A enzyme activity at TKT using an in vitro fluorescence assay. Serum/plasma concentration profiles were analyzed using a non-compartmental model to estimate pharmacokinetic parameters.

Predose enzyme activity averaged 1.2 U/ml in males and 6.5 U/ml in females which reflects the carrier status of female patients (Table 7).

Figure 15:
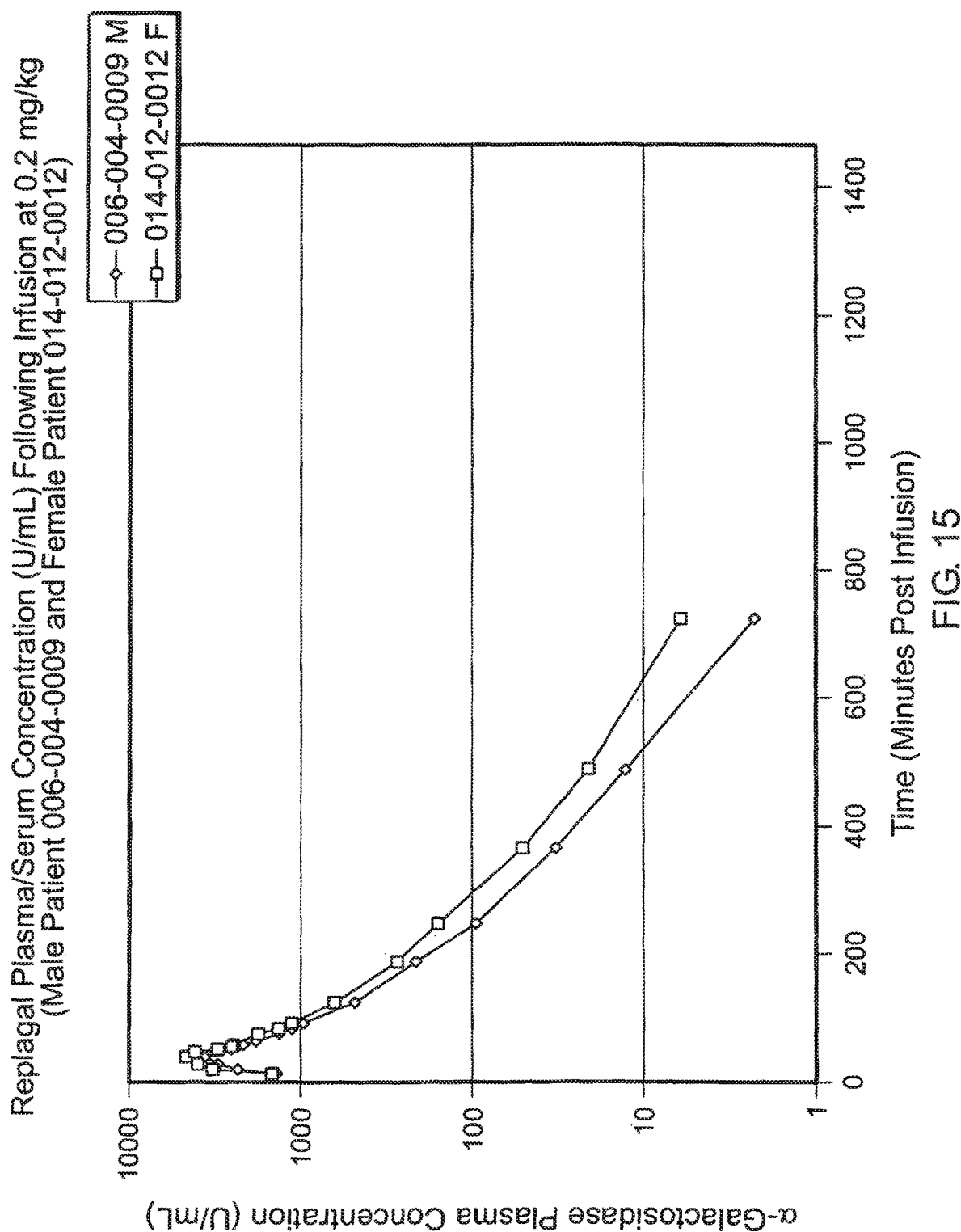
FIG. 15 is a graph showing Replagal™ plasma concentration (U/ml) following infusion at 0.2 mg/kg in a male and female human subject.
Figure 16:
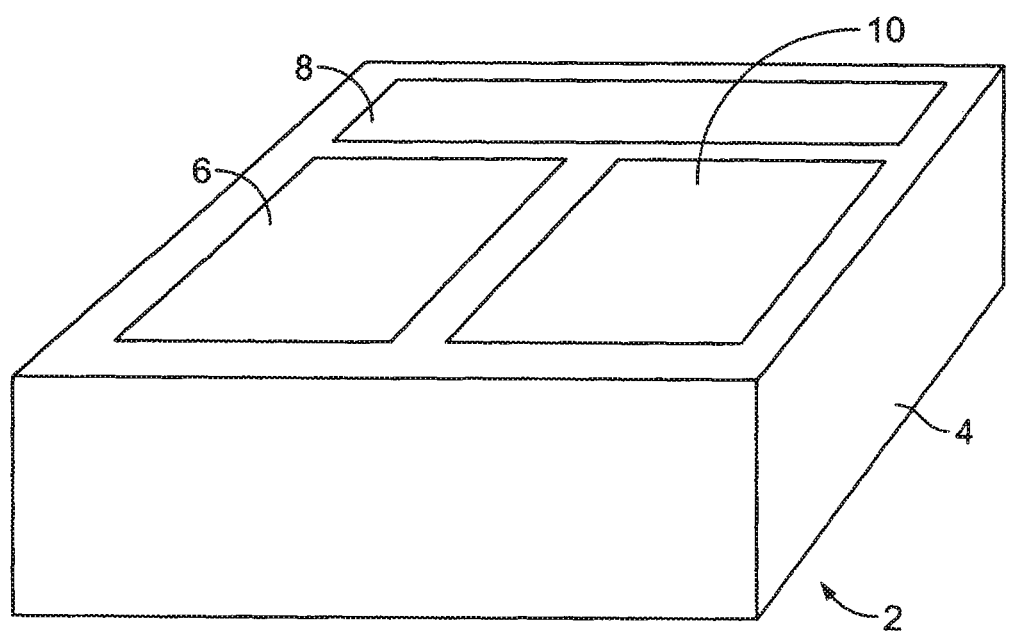
FIG. 16 is a schematic drawing of a kit containing an α-Gal A preparation described herein packaged in a vial and instructions for administering the preparation.

Replagal™ had a biphasic serum elimination profile following a single intravenous infusion in both male and female Fabry patients and was eliminated from most patients by 24 hours after dosing (FIG. 15). As expected, $C_{max}$ coincided with the end of the 40 minute infusion period.

Mean pharmacokinetic parameters were similar between male and female patients (Table 8). AUC (area under the curve) normalized for dose was slightly greater in females (ratio of 0.51) but was not statistically different from the male ration (0.43). Absolute serum clearance of Replagal™ was lower in females (140 compared to 177 mL/min); but when normalized for body weight, serum clearance was not statistically different (2.10 versus 2.52 mL/min/kg). The statistically significant difference in terminal elimination half-life (89 minutes in females versus 112 minutes in males) was not due to a difference in elimination of Replagal™ from females. Instead, the higher baseline enzyme activity in women made it difficult to detect adminstered Replagal™ beyond 8 hours ($T_{fast}$).

Clearance of Replagal™ from the circulation of Fabry patients was more rapid than individual patient GFR or creatinine clearance which is consistent with its mechanism of clearance (Table 9). Replagal™ is primarily cleared from the circulation by uptake into tissues via mannose-6-phosphate (M6P) receptors and minimally by protein degradation and kidney elimination.

An analysis was performed to confirm that changes in renal function will not affect clearance of Replagal™ from the circulation (Table 10). Most of the Fabry patients undergoing first dose pharmacokinetic analysis were either in the normal range (>80 mL/min creatine clearance) or had "mild" renal impairment (50-80 mL/min creatine clearance) when they received their first dose of Replagal™. Although only 5 patients were in the moderate or severe categories, serum clearance of Replagal (ml/min/kg) for these patients was within the range established by the 2 higher renal function categories. These data suggest that Replagal™ is not excreted by the kidney. There were no differences between males and females in this analysis.

Serum clearance of Fabrazyme™ from Fabry patients was significantly more rapid compared to that observed with Replagal™ (Table 11). At nearly equal doses in male patients (0.2 and 0.3 mg/kg for Replagal and Fabrazyme, respectively), serum clearance of Fabrazyme™ was 4 mL/min/kg compared to 2.5 mL/min/kg for Replagal™. This difference in serum clearance at nearly equivalent doses is due to the different glycosylation pattern of Fabrazyme™ (manufactured in CHO cells) compared to the human glycosylation pattern of Replagal™. At higher doses of Fabrazyme™ (1 and 3 mg/kg), serum clearance was significantly reduced to approximately 2.7 and 1 mL/min/kg as clearance mechanisms became saturated for Fabrazyme™.

Thus, pharmacokinetic parameters were similar in male and female patients dosed with Replagal™. Serum clearance of Replagal™ significantly exceeded renal function (mL/min), consistent with M6P mediated uptake of Replagal™ into tissues and cells throughout the body. As expected, preliminary analysis indicated that Replagal is not excreted by the kidney. At doses below clearance saturation levels, Fabrazyme™ scrum clearance was significantly more rapid compared to Replagal™ and reflects differences in glycosylation patterns between the two drug products.

TABLE 1

|  | Replagal | Fabrazyme |
| --- | --- | --- |
| Neutral | 15.6% | 4.6% |
| 1 Sialic Acid | 29.5% | 8.9% |
| Unknown | 4.6% | 1.8% |
| 2 Sialic Acid | 20.1% | 11.3% |
| 1 Phosphate | 13.0% | 27.1% |
| Unknown | 4.0% | 4.6% |
| 3 Sialic Acid | 1.9% | 8.5% |
| 4 Sialic Acid | 5.9% | 15.1% |
| 2 Phosphate | 5.4% | 18.0% |

TABLE 2

| Sample ID | % Neutrals | %1 Charges | %2 Charges | %3 Charges | %4 Charges |
| --- | --- | --- | --- | --- | --- |
| CK-022 vial 1 | 32.76 | 26.97 | 25.64 | 9.78 | 4.85 |
| CK-022 vial 2 | 33.61 | 26.37 | 25.16 | 9.92 | 4.93 |
| CK-006 vial 1 | 29.73 | 25.61 | 27.12 | 11.85 | 5.70 |
| CK-006 vial 2 | 29.33 | 26.69 | 27.14 | 11.47 | 5.37 |

TABLE 2-continued

| Sample ID | % Neutrals | %1 Charges | %2 Charges | %3 Charges | %4 Charges |
|---|---|---|---|---|---|
| CK-JL012502 vial 1 | 21.88 | 12.59 | 38.44 | 21.94 | 5.15 |
| CK-JL012502 vial 2 | 21.60 | 12.61 | 39.35 | 21.44 | 5.00 |

TABLE 3

| Sample ID | % Neutrals | %1 Charges | %2 Charges |
|---|---|---|---|
| CK-022 inj 1 | 94.45 | 2.73 | 2.82 |
| CK-022 inj 2 | 94.39 | 2.68 | 2.93 |
| CK-006 inj 1 | 93.18 | 2.57 | 4.25 |
| CK-006 inj 2 | 93.34 | 2.24 | 4.42 |
| CK-JL012502 inj 1 | 88.52 | 4.37 | 7.11 |
| CK-JL012502 inj 2 | 88.08 | 4.41 | 7.51 |

TABLE 4

Allometri Scaling of Physiological and Anatomical Parameters (function of body weight, BW)
Equation: $Y = a (BW)^b$

| Parameter (Y) | Exponent (b) |
|---|---|
| Body surface area | 0.67 |
| Blood volume (mL) | 0.99 |
| Lung weight (g) | 0.99 |
| Urine output (mL/h) | 0.82 |
| Insulin clearance (mL/h) | 0.77 |
| Kidney weight (g) | 0.85 |
| Drug Clearance from Plasma | 0.6-0.8 |
| Protein Clearance from Plasma | 0.65-0.84 |
| M6P Receptor Clearance | ? |

Chappell and Mordenti (1991) Extrapolation of Toxicological and Pharmacological Data from Animals to Humans. In B. Testa (ed.) *Advances in Drug Research*, Vol. 20, pp. 1-116.

TABLE 5

Allometric Scaling of Pharmacokinetic Parameters - Exponents

| Drug Product | Cl (mL/min) |
|---|---|
| Small molecules* | 0.6-0.8 |
| Published proteins* | 0.65-0.84 |
| Rt-PA | 0.84 |
| Relaxin | 0.80 |
| CD4-IgG | 0.74 |
| rhGH | 0.71 |
| RCD4 | 0.65 |
| Replagal ™ | 0.92 |

*Mordenti et al. (1991) Interspecies Scaling of Clearance and Volume Distribution Data for Five Therapeutic Proteins. *Pharmaceutical Research* 8: 1351-1359.

TABLE 6

Percent Administered Dose of Replagal in Human Liver

| | | | Percent administered Dose in Liver | |
|---|---|---|---|---|
| Dose (mg/kg) | Infusion Time | $C_{max}$ ($\times 10^{-9}$ M) | 44 Hr (measured) | $T_{max}$ (2 hours) claculated using $T_{1/2}$ of 3 Days |
| 0.007 | 20 min | 0.4 | 25.0% | 38% |
| 0.014 | 20 min | 1.1 | 28.7% | 43% |
| 0.028 | 20 min | 2.5 | 16.8% | 25% |
| 0.056 | 20 min | 5.0 | 19.4% | 29% |
| 0.11 | 20 min | 7.8 | 13.7% | 21% |
| 0.2 | 40 min | 11.6 | not determined | 8%-18% (estimate) |

M6P receptor Kd is $2 \times 10^{-9}$ M (Kornfeld *Ann Rev Biochem* 61: 307-330, 1992)
α-Galactosidase A half-lives:
4 days in Fabry fibroblasts (Mayes et al., *Am J Hum Genet* 34: 602-610, 1982)
2 days in mouse liver (Ioannou et al., *Am J Hum Genet* 68: 14-25, 2001)

TABLE 7

Baseline Values of α-Galactosidase A Enzyme Activity

| Study No. | No. of Patients | Average Baseline Value (U/mL) |
|---|---|---|
| TKT006 and TKT007 (NIH and UK) | 39 males | 1.2* (range 0.4-9) |
| TKT014 (Germany) | 15 females | 6.5 (range 2-12) |

*excludes one male patient with a baseline value of approximately 15 U/mL
1 Unit (U) is defined as the hydrolysis of one nanomole of 4-methylumbelliferyl-α-D-galactopyranoside per hour at 37° C.

TABLE 8

Pharmacokinetic Comparison between Male and Female Fabry Patients Following 1st Dose of Replagal

| Clinical Study | No. | Avg Dose (U/kg × $10^6$) | Body Wt (kg) | AUC/Dose | Cl (mL/min) | Cl (mL/min/kg) | $T_{1/2}$ ($\lambda_z$) (min) | Median $T_{last}$ | $V_{ss}$ (% BW) |
|---|---|---|---|---|---|---|---|---|---|
| TKT006 TKT007 | 18 males | 0.61 | 72.9 (16.1) | 0.43 (0.12) | 177 (43) | 2.52 (0.74) | 112 (25) | 12 hours | 16.0% (4.3%) |
| TKT014 | 15 females | 0.66 | 68.0 (13.8) | 0.51 (0.13) | 140 (38) | 2.10 (0.62) | 89 (28) | 8 hours | 16.5% (4.3%) |
| | t-test | | | 0.057 | 0.015 | 0.10 | 0.02 | NA | NS |

( ) standard deviation

NA, not applicable

NS, not significant $T_{last}$, time of last detectable Replagal enzyme activity Normalized AUC has units of (min*U/mL)/(U/kg)

TABLE 9

Serum Clearance of Replagal from Male and Female Patients

| Study No. | Pharmacokinetic Evaluation (N) | Mean GFR* (mL/min) | Mean Replagal Clearance (mL/min) |
|---|---|---|---|
| TKT006 (NIH) | 10 males | 78 (24) | 193 (47) |
| TKT005 (UK) | 8 males | 115 (63) | 157 (29) |
| Combined | 18 males | 95 (48) | 177 (43) |
| TKT014 (Germany) | 15 females | 70 (20) † | 140 (38) |

( ) standard deviation
N, number of patients evaluated for pharmacokinetic parameters following first dose of Replagal
*GFR, glomerular filtration rate, measured 2-3 weeks before first dose of Replagal
† creatinine clearance measured in female

TABLE 10

Comparison of Renal Function and Replagal Serum Clearance

| Study No. | Pharmacokinetic Evaluation (N) | Real Function Category* | Range of Replagal Clearance (mL/min/kg) |
|---|---|---|---|
| TKT006 (NIH) and TKT007 (UK) | 10 males | Normal Range (>80 mL/min) | 1.7-3.4 |
| | 6 males | Mild (50-80 mL/min) | 2.0-4.4 |
| | 1 males | Moderate (30-50 mL/min) | 3.5 |
| | 1 males | Severe <30 mL/min | 1.6 |
| TKT014 (Germany) | 5 females | Normal Range (>80 mL/min) | 2.2-3.0 |
| | 7 females | Mild (50-80 mL/min) | 1.4-3.6 |
| | 2 females | Moderate (30-50 mL/min) | 1.5-1.6 |
| | 1 females | Severe (<30 mL/min) | 1.8 |

*FDA categories based on estimated creatinine clearance

TABLE 11

Serum Clearance in Fabry Patients Dosed with Replagal or Fabrazyme

| | Serum Clearance (mL/min/kg) | | |
|---|---|---|---|
| Dose | Fabrazyme | Replagal | |
| (mg/kg) | Males* | Males | Females |
| 0.2 | | 2.5 | 2.1 |
| 0.3 | 4 | | |
| 1.0 | ~2.7 † | | |
| 3.0 | ~1 † | | |

*Eng et al (2001) A Phase I/II Clinical Trial of Enzyme Replacement in Fabry Disease. *Am J Hum Genet* 68: 711-722.
† serum clearance saturated

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety. What is claimed is presented below and is followed by a Sequence Listing.

We claim:

1. A method of treating α-Gal A deficiency in a subject in need thereof, comprising:
providing or obtaining one or more human α-Gal A glycoprotein preparations;
selecting an α-Gal A preparation having biological or pharmacokinetic characteristics (a) and (b), wherein the characteristics are (a) a serum clearance of the α-Gal A preparation from the subject's circulation of less than 4 mL/min/kg on the linear portion of the AUC vs. dose curve when the preparation is administered at a unit dose of less than 1.0 mg per kilogram of body weight of the subject; and (b) the a-Gal A glycoprotein is targeted to capillary/vascular endothelial cells, renal glomerular epithelial cells and glomerular mesangial cells, renal endothelial cells, cardiac myocytes, liver endothelial cells, liver sinusoidal cells, pulmonary cells, or neural cells, and
administering one or more doses of a therapeutically effective amount of the selected preparation to the subject.

2. The method of claim 1, wherein serum clearance of the α-Gal A preparation from the subject's circulation is 3.5 mL/min/kg or less on the linear portion of the AUC vs. dose curve.

3. The method of claim 1, wherein serum clearance of the α-Gal A preparation from the subject's circulation is 3.0 mL/min/kg or less on the linear portion of the AUC vs. dose curve.

4. The method of claim 1, wherein serum clearance of the α-Gal A preparation from the subject's circulation is 2.5 mL/min/kg or less on the linear portion of the AUC vs. dose curve.

5. The method of claim 1, wherein the human α-Gal A glycoprotein preparation is administered at a unit dose of less than 1.0 mg per kilogram of body weight of the subject.

6. The method of claim 5, wherein the unit dose is less than 0.5 mg per kilogram of body weight of the subject.

7. The method of claim 5, wherein the unit dose is less than 0.3 mg per kilogram of body weight of the subject.

8. The method of claim 5, wherein the unit dose is less than 0.25 mg per-kilogram of body weight of the subject.

9. The method of claim 5, wherein the unit dose is less than 0.2 mg per kilogram of body weight of the subject.

10. The method of claim 5, wherein the unit dose is administered no more than once every 8 weeks.

11. The method of claim 10, wherein the preparation is administered for at least 1 year.

12. The method of claim 5, wherein the unit dose is administered no more than once every 6 weeks.

13. The method of claim 12, wherein the preparation is administered for at least 1 year.

14. The method of claim 5, wherein the unit dose is administered no more than once every 4 weeks.

15. The method of claim 14, wherein the preparation is administered for at least 1 year.

16. The method of claim 5, wherein the unit dose is administered no more than once every 21 days.

17. The method of claim 16, wherein the preparation is administered for at least 1 year.

18. The method of claim 5, wherein the unit dose is administered no more than once every 14 days.

19. The method of claim 1, wherein the human α-Gal A glycoprotein preparation is administered no more than once every 14 days.

20. The method of claim 19, wherein the preparation is administered no more than once every 4 weeks.

21. The method of claim 19, wherein the preparation is administered no more than once every 6 weeks.

22. The method of claim 19, wherein the preparation is administered no more than once every 8 weeks.

23. The method of claim 19, wherein the unit dose of the administration is less than 0.5 mg per kilogram of body weight.

24. The method of claim 19, wherein the unit dose of the administration is less than 0.3 mg per kilogram of body weight.

25. The method of claim 19, wherein the unit dose saturates liver uptake of the α-Gal A.

* * * * *

SEQUENCE LISTING

```
<160> NUMBER OF SEQ ID NOS: 2

<210> SEQ ID NO 1
<211> LENGTH: 1343
<212> TYPE: DNA
<213> ORGANISM: Homo sapiens

<400> SEQUENCE: 1
ccgcgggaaa tttatgctgt ccggtcaccg tgacaatgca gctgaggaac ccagaactac        60
atctgggctg cgcgcttgcg cttcgcttcc tggccctcgt ttcctgggac atccctgggg       120
ctagagcact ggacaatgga ttggcaagga cgcctaccat gggctggctg cactgggagc       180
gcttcatgtg caaccttgac tgccaggaag agccagattc ctgcatcagt gagaagctct       240
tcatggagat ggcagagctc atggtctcag aaggctggaa ggatgcaggt tatgagtacc       300
tctgcattga tgactgttgg atggctcccc aaagagattc agaaggcaga cttcaggcag       360
accctcagcg ctttcctcat gggattcgcc agctagctaa ttatgttcac agcaaaggac       420
tgaagctagg gatttatgca gatgttggaa ataaaacctg cgcaggcttc cctgggagtt       480
ttggatacta cgacattgat gcccagacct ttgctgactg gggagtagat ctgctaaaat       540
ttgatggttg ttactgtgac agtttggaaa atttggcaga tggttataag cacatgtcct       600
tggccctgaa taggactggc agaagcattg tgtactcctg tgagtggcct ctttatatgt       660
ggccctttca aaagcccaat tatacagaaa tccgacagta ctgcaatcac tggcgaaatt       720
ttgctgacat tgatgattcc tggaaaagta taaagagtat cttggactgg acatctttta       780
accaggagag aattgttgat gttgctggac caggggttg gaatgaccca gatatgttag       840
```

```
tgattggcaa ctttggcctc agctggaatc agcaagtaac tcagatggcc ctctgggcta    900
tcatggctgc tcctttattc atgtctaatg acctccgaca catcagccct caagccaaag    960
ctctccttca ggataaggac gtaattgcca tcaatcagga ccccttgggc aagcaagggt    1020
accagcttag acagggagac aactttgaag tgtgggaacg acctctctca ggcttagcct    1080
gggctgtagc tatgataaac cggcaggaga ttggtggacc tcgctcttat accatcgcag    1140
ttgcttccct gggtaaagga gtggcctgta atcctgcctg cttcatcaca cagctcctcc    1200
ctgtgaaaag gaagctaggg ttctatgaat ggacttcaag gttaagaagt cacataaatc    1260
ccacaggcac tgttttgctt cagctagaaa atacaatgca gatgtcatta aaagacttac    1320
tttaaaaaaa aaaaaaactc gag                                            1343
```

<210> SEQ ID NO 2
<211> LENGTH: 398
<212> TYPE: PRT
<213> ORGANISM: Homo sapiens

<400> SEQUENCE: 2

```
Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285
```

```
Asn Gln Asp Pro Leu Gly Lys Gln Gly Tyr Gln Leu Arg Gln Gly Asp
        290                 295                 300

Asn Phe Glu Val Trp Glu Arg Pro Leu Ser Gly Leu Ala Trp Ala Val
305                     310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
                340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
        370                 375                 380

Gln Leu Glu Asn Thr Met Gln Met Ser Leu Lys Asp Leu Leu
385                 390                 395
```